United States Patent
McKay et al.

(10) Patent No.: US 6,187,545 B1
(45) Date of Patent: Feb. 13, 2001

(54) ANTISENSE MODULATION OF PEPCK-CYTOSOLIC EXPRESSION

(75) Inventors: Robert McKay, San Diego; Madeline M. Butler, Santa Fe; Jacqueline Wyatt, Encinitas; Lex M. Cowsert, Carlsbad, all of CA (US)

(73) Assignee: Isis Pharmaceuticals Inc., Carlsbad, CA (US)

( * ) Notice: Under 35 U.S.C. 154(b), the term of this patent shall be extended for 0 days.

(21) Appl. No.: 09/488,671

(22) Filed: Jan. 21, 2000

(51) Int. Cl.$^7$ .............................. C07A 21/04; C12Q 1/68; C12N 15/85
(52) U.S. Cl. .............................. 435/6; 435/91.1; 435/325; 536/24.5
(58) Field of Search .................................. 514/44; 435/6, 435/91.1, 325; 536/23.1, 24.5

(56) References Cited

U.S. PATENT DOCUMENTS 5,580,722 * 12/1996 Foulkes et al. ........................... 435/6
5,789,573 * 8/1998 Baker et al. ......................... 536/24.5

OTHER PUBLICATIONS

Williams et al., Genbank Accession # AF009605, Jun. 1997.*
Stoffel et al., Genbank Accession # L05144, 1993.*
Branch, A good antisense is hard to find, TIBS, vol. 23, pp. 45–50, Feb. 1998.*
Agrawal, Antisense oligonucleotides: towards clinical trials, TIBTECH, vol. 14, pp. 376–387, Oct. 1996.*
Gewirtz et al., Facilitating oligonucleotide delivery: helping antisense deliver on its promise, PNAS, vol. 93, pp. 3161–3163, Apr. 1996.*
Agati et al., Assessment of the roles of mitogenactivated protein kinase, phosphatidylinositol 3–kinase, protein kinase B, and protein kinase C in insulin inhibition of cAMP–induced phosphoenolpyruvate carboxykinase gene transcription, *J. Biol. Chem.*, 1998, 273:18751–18759.
Beale et al., Cell–specific expression of cytosolic phosphoenolpyruvate carboxykinase in transgenic mice, *Faseb J.*, 1992, 6:3330–3337.
Christ et al., Impairment by interleukin 1 beta and tumour necrosis factor alpha of the glucagon–induced increase in phosphoenolpyruvate carboxykinase gene expression and gluconeogenesis in cultured rat hepatocytes [published erratum appears in Biochem J 1997 Feb 1;321 (Pt 3) :903], *Biochem. J.*, 1996, 320:161–166.

Christ et al., Mechanism of the impairment of the glucagon–stimulated phosphoenolpyruvate carboxykinase gene expression by interleukin–6 in rat hepatocytes:inhibition of the increase in cyclic 3',5' adenosine monophosphate and the downstream cyclic 3',5' adenosine monophosphate action, *Hepatology*, 1997, 26:73–80.

Hanson et al., Phosphoenolpyruvate carboxykinase (GTP): the gene and the enzyme, *Adv. Enzymol. Relat. Areas Mol. Biol.*, 1994, 69:203–281.

Hanson et al., Regulation of phosphoenolpyruvate carboxykinase (GTP) gene expression, *Annu. Rev. Biochem.*, 1997, 66:581–611.

Kaiser, Cell volume regulates liver phosphoenolpyruvate carboxykinase and fructose–1,6–bisphosphatase genes, *Am. J. Physiol.*, 1998, 274:G509–517.

Kietzmann et al., Diminution of the O2 responsiveness of the glucagon–dependent activation of the phosphoenolpyruvate carboxykinase gene in rat hepatocytes by long–term culture at venous PO2, Kidney Int., 1997, 51:542–547.

Kietzmann et al., Regulation of the gluconeogenic phosphoenolypruvate carboxykinase and glycolytic aldolase A gene expression by O2 in rat hepatocyte cultures. Involvement of hydrogen peroxide as mediator in the response to O2, *FEBS Lett.*, 1996, 388:228–232.

Sutherland et al., New connections in the regulation of PEPCK gene expression by insulin, *Philos. Trans. R. Soc. Lond. B. Biol. Sci.*, 1996, 351:191–199.

* cited by examiner

Primary Examiner—Robert A. Schwartzman
Assistant Examiner—Andrew Wang
(74) Attorney, Agent, or Firm—Law Offices of Jane Massey Licata

(57) ABSTRACT

Antisense compounds, compositions and methods are provided for modulating the expression of PEPCK-cytosolic. The compositions comprise antisense compounds, particularly antisense oligonucleotides, targeted to nucleic acids encoding PEPCK-cytosolic. Methods of using these compounds for modulation of PEPCK-cytosolic expression and for treatment of diseases associated with expression of PEPCK-cytosolic are provided.

10 Claims, No Drawings

ANTISENSE MODULATION OF PEPCK-CYTOSOLIC EXPRESSION

FIELD OF THE INVENTION

The present invention provides compositions and methods for modulating the expression of PEPCK-cytosolic. In particular, this invention relates to antisense compounds, particularly oligonucleotides, specifically hybridizable with nucleic acids encoding PEPCK-cytosolic. Such oligonucleotides have been shown to modulate the expression of PEPCK-cytosolic.

BACKGROUND OF THE INVENTION

Gluconeogenesis is the metabolic pathway for the biosynthesis of glucose from non-carbohydrate precursors including pyruvate, lactate, and citric acid cycle intermediates. This pathway occurs predominantly in the liver and to a lesser extent in the kidney and is triggered by a fall in blood glucose concentration. Gluconeogenesis meets the needs of the body for glucose when there is insufficient intake of carbohydrates in the diet. It is also critical to the maintenance of a continuous energy supply, in the form of glucose, to red blood cells and tissues of the central nervous system, which do not undergo gluconeogenesis. In addition, gluconeogenesis represents a mechanism by which products of metabolism from other tissues are cleared from the blood and converted back into glucose. Under fasting conditions glucose production through this pathway maintains the basal glucose concentrations necessary to sustain primary physiologic functions. The gluconeogenic pathway is essentially glycolysis (the breakdown of glucose received predominantly from the diet) in reverse. There are four enzymes necessary to bypass the thermodynamically unfavorable steps of glycolysis. These enzymes are pyruvate carboxylase, phosphoenolpyruvate carboxykinase, fructose-1,6-bisphosphatase, and glucose-6-phosphatase. The rate-limiting step of gluconeogenesis is catalyzed by phosphoenolpyruvate carboxykinase and this enzyme has been well characterized in several species. Two forms (isozymes) of the enzyme have been isolated and the total enzyme activity displayed in humans is equally divided between the cytosolic and mitochondrial forms (Hanson and Patel, *Adv. Enzymol. Relat. Areas Mol. Biol.,* 1994, 69, 203–281).

Cytosolic phosphoenolpyruvate carboxykinase (also known as PCK1, cyPCK and PEPCK-C) is expressed predominantly in liver where it acts in the gluconeogenic pathway and in kidney where it acts in the gluconeogenic pathway as well as being glyceroneogenic and ammoniagenic (Hanson and Reshef, *Annu. Rev. Biochem.,* 1997, 66, 581–611). PEPCK-cytosolic also exhibits significant expression in white and brown adipose tissue, lactating mammary gland and the small intestine where it is thought to supply glycerol for triglyceride synthesis (glyceroneogenesis) in these tissues (Hanson and Reshef, *Annu. Rev. Biochem.,* 1997, 66, 581–611).

Studies using transgenic mice have shown that different cis acting elements are required to drive the expression of PEPCK-cytosolic in hepatocytes, renal tubule epithelial cells and adipocytes (Beale et al., Faseb J., 1992, 6, 3330–3337).

The overall expression of PEPCK-cytosolic is controlled entirely at the level of transcription by a wide variety of physiological stimuli including dietary carbohydrate, hormones, and cellular intermediates (Hanson and Patel, *Adv. Enzymol. Relat. Areas Mol. Biol.,* 1994, 69, 203–281). It is expressed in the periportal region of the liver and is therefore sensitive to oxygen concentration. Studies of rat hepatocytes demonstrated that the glucagon-dependent activation of the PEPCK-cytosolic gene is modulated by oxygen and that this process is mediated by hydrogen peroxide (Kietzmann et al., *Kidney Int.,* 1997, 51, 542–547; Kietzmann et al., FEBS Lett., 1996, 388, 228–232). Other factors have also been shown to impair the glucagon-induced increase in PEPCK-cytosolic including interleukin-1-beta, tumor necrosis factor alpha and interleukin-6 (Christ and Nath, *Biochem. J.,* 1996, 320, 161–166; Christ et al., *Hepatology,* 1997, 26, 73–80).

In the liver, PEPCK-cytosolic is negatively regulated by insulin and has therefore been considered a potential contributing factor to hyperglycemia in diabetics (Sutherland et al., *Philos. Trans. R. Soc. Lond. B. Biol. Sci.,* 1996, 351, 191–199). Studies using various kinase inhibitors demonstrated a link between PEPCK-cytosolic gene regulation by insulin and the protein kinase phosphatidylinositol-3-kinase (PI3-kinase). In these studies, it was shown that insulin inhibition of PEPCK-cytosolic gene expression requires PI3-kinase but that the signal is not mediated by MAP kinases nor transmitted through protein kinase B or protein kinase C (Agati et al., *J. Biol. Chem.,* 1998, 273, 18751–18759; Sutherland et al., *Philos. Trans. R. Soc. Lond. B. Biol. Sci.,* 1996, 351, 191–199).

PEPCK-cytosolic gene expression is also sensitive to other regulatory stimuli including cell volume. It has been shown that in rat and human hepatocytes, changes in cell volume alter the rate of transcription and mRNA stability of PEPCK-cytosolic (Kaiser, *Am. J. Physiol.,* 1998, 274, G509–517).

Currently, there are no known therapeutic agents which effectively inhibit the synthesis of PEPCK-cytosolic and to date, strategies aimed at investigating PEPCK-cytosolic function have involved the use of chemical inhibitors and transgenic mice.

Consequently, there remains a long felt need for agents capable of effectively inhibiting PEPCK-cytosolic function.

Antisense technology is emerging as an effective means for reducing the expression of specific gene products and may therefore prove to be uniquely useful in a number of therapeutic, diagnostic, and research applications for the modulation of PEPCK-cytosolic expression.

SUMMARY OF THE INVENTION

The present invention is directed to antisense compounds, particularly oligonucleotides, which are targeted to a nucleic acid encoding PEPCK-cytosolic, and which modulate the expression of PEPCK-cytosolic. Pharmaceutical and other compositions comprising the antisense compounds of the invention are also provided. Further provided are methods of modulating the expression of PEPCK-cytosolic in cells or tissues comprising contacting said cells or tissues with one or more of the antisense compounds or compositions of the invention. Further provided are methods of treating an animal, particularly a human, suspected of having or being prone to a disease or condition associated with expression of PEPCK-cytosolic by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding PEPCK-cytosolic, ultimately modulating the amount of PEPCK-cytosolic produced. This is accomplished by providing antisense compounds which specifically hybridize with one or more nucleic acids encoding PEPCK-cytosolic. As used herein, the terms "target nucleic acid" and "nucleic acid encoding PEPCK-cytosolic" encompass DNA encoding PEPCK-cytosolic, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PEPCK-cytosolic. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PEPCK-cytosolic. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PEPCK-cytosolic, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation 3termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease.

Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages.

As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564;

5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference.

Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$), ONH$_2$ and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—CH$_2$CH$_2$OCH$_3$, also known as 2'—O—(2-methoxyethyl) or 2'—MOE) (Martin et al., *Helv. Chim. Acta,* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'—DMAOE, as described in examples hereinbelow, and 2'-dimethylaminoethoxyethoxy (also known in the art as 2'—O—dimethylaminoethoxyethyl or 2$^1$-DMAEOE), i.e., 2'—O—CH$_2$—O—CH$_2$—N(CH$_2$)$_2$, also described in examples hereinbelow.

Other preferred modifications include 2'-methoxy (2'—O—CH$_3$), 2'-aminopropoxy (2'—OCH$_2$CH$_2$CH$_2$NH$_2$) and 2'-fluoro (2'—F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering,* pages 858–859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Chapter 15, *Antisense Research and Applications,* pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications,* CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al.,*Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al. ,3. The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of PEPCK-cytosolic is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PEPCK-cytosolic, enabling sandwich and other assays to easily be constructed to exploit this fact. Hybridization of the antisense oligonucleotides of the invention with a nucleic acid encoding PEPCK-cytosolic can be detected by means known in the art. Such means may include conjugation of an enzyme to the oligonucleotide, radiolabelling of the oligonucleotide or any other suitable detection means. Kits using such detection means for detecting the level of PEPCK-cytosolic in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.
Emulsions The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in –Pharmaceutical Dosage Forms,Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274). One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasomem II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$. or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone. Carriers Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1
Nucleoside Phosphoramidites for Oligonucleotide Synthesis
Deoxy and 2'-alkoxy amidites 2'-Deoxy and 2'-methoxy beta-cyanoethyldiisopropyl phosphoramidites were purchased from commercial sources (e.g. Chemgenes, Needham MA or Glen Research, Inc. Sterling Va.). Other 2'-O-alkoxy substituted nucleoside amidites are prepared as described in U.S. Pat. No. 5,506,351, herein incorporated by reference. For oligonucleotides synthesized ,using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective 0-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% c hydrogen fluoride-pyridine. Standard procedures were used to obtain the 5'-DMT and 5'-DMT-3' phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured 2into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 23500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/hexane/acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH3 gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L).

Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylazinooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution aof hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.BmL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.lg, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5,–0-tert-butyldiphenylsilyl-2'-O-[(2-formadoximinooxy) ethyl]-5-methyluridine as white foam (1.95 g, 78%).

5'-O-tort-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.Ommol) was dissolved in dry THF and triethylamine (1.67 mL, 12 mmol, dry, kept over KOH). This mixture of triethylamine-2HF was then added to 5,–0-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%). 5'-O-DKT-2'-O-(dimethylaminooxyethyl)-5-methyluridine 2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-0-diphenylcarbamoyl-2'-O-(2-ethylacetyl)-5'-O-(4,4'-dimethoxytrityl)guanosine which may be reduced to provide 2-N-isobutyryl-6-0-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may be phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'—O—CH$_2$—O—CH$_2$—N (CH$_2$) 2, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O2,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl uridine To 0.5 g (1.3 imol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me]Chimeric
Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate
Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy
Phosphorothioate]—[2'-O-(2-Methoxyethyl)
Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell culture and oligonucleotide treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 cells:

The human transitional cell bladder carcinoma cell line T-24 was obtained from the American Type Culture Collection (ATCC) (Manassas, VA). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HepG2 cells:

The human hepatoblastoma cell line HepG2 was obtained from the American Type Culure Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

Primary mouse hepatocytes

Primary mouse hepatocytes were prepared from CD-1 mice purchased from Charles River Labs. Primary mouse hepatocytes were routinely cultured in Hepatoyte Attachment Media (Gibco) supplemented with 10% Fetal Bovine Serum (Gibco/Life Technologies, Gaithersburg, Md.), 250nM dexamethasone (Sigma), 10 nM bovine insulin (Sigma). Cells were seeded into 96-well plates (Falcon-Primaria #3872) at a density of 10000 cells/well for use in RT-PCR analysis.

For Northern blotting or other analysis, cells may be seeded onto 100 mm or other standard tissue culture plates =and treated similarly, using appropriate volumes of medium and oligonucleotide.

Treatment with antisense compounds:

When cells reached 80% confluency, they were treated with oligonucleotide. For cells grown in 96-well plates, wells were washed once with 200 gL OPTI-MEMTM-1 reduced-serum medium (Gibco BRL) and then treated with 130 gL of OPTI-MEMTM-1 containing 3.75 μg/mL LIPO-FECTINTM (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of oligonucleotide inhibition of PEPCK-cytosolic expression

Antisense modulation of PEPCK-cytosolic expression can be assayed in a variety of ways known in the art. For example, PEPCK-cytosolic mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of PEPCK-cytosolic can be quantitated in a variety of ways well known in the art, such as immunoprecipitation, Western blot analysis (immunoblotting), ELISA or fluorescence-activated cell sorting (FACS). Antibodies directed to PEPCK-cytosolic can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+mRNA isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY $_{96}$Tm kit and buffers purchased from Qiagen Inc. (Valencia CA) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVACT manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-time Quantitative PCR Analysis of PEPCK-cytosolic mRNA Levels Quantitation of PEPCK-cytosolic mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, CA or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1× TAQMAN™ buffer A, 5.5 mM $MgCl_2$, 300 μM each of dATP, dCTP and dGTP, 600 μM of dUTP, 100 μM each of forward primer, reverse primer, and probe, 20 Units RNAse inhibitor, 1.25 Units AMPLITAQ GOLD™, and 12.5 Units MULV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human PEPCK-cytosolic were designed to hybridize to a human PEPCK-cytosolic sequence, using published sequence information (GenBank accession number L05144, incorporated herein as SEQ ID NO:3). For human PEPCK-cytosolic the PCR primers were: forward primer: TGGGCTCACCTCTGTCGAA (SEQ ID NO: 4) reverse primer: TGCCCATCCGCGTCAT (SEQ ID NO: 5) and the PCR probe was: FAM-CTGACGGATTCGCCCTACGTGGTG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse PEPCK-cytosolic were designed to hybridize to a mouse PEPCK-cytosolic sequence, using published sequence information (GenBank accession number AF009605, incorporated herein as SEQ ID NO:10). For mouse PEPCK-cytosolic the PCR primers were: forward primer: ATCCAGGGCAGCCTCGA (SEQ ID NO:11) reverse primer: AGCATTGCCTTCCAC-GAACT (SEQ ID NO: 12) and the PCR probe was: FAM-AGCCTGCCCCAGGCAGTGAGG-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGCT (SEQ ID NO: 15) and the PCR probe was: 5' JOE-AAGGCCGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14
Northern blot analysis of PEPCK-cytosolic mRNA levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYBT hybridization solution (Stratagene, La Jolla, Calif.) using manufacturer's recommendations for stringent conditions.

To detect human PEPCK-cytosolic, a human PEPCK-cytosolic specific probe was prepared by PCR using the forward primer TGGGCTCACCTCTGTCGAA (SEQ ID NO: 4) and the reverse primer TGCCCATCCGCGTCAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse PEPCK-cytosolic, a mouse PEPCK-cytosolic specific probe was prepared by PCR using the forward primer ATCCAGGGCAGCCTCGA (SEQ ID NO:11) and the reverse primer AGCATTGCCTTCCAC-GAACT (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense inhibition of human PEPCK-cytosolic expression by chimeric phosphorothioate oligonucleotides having 2'-MOE wings and a deoxy gap In accordance with the present invention, a series of oligonucleotides were designed to target different regions of the human PEPCK-cytosolic RNA, using published sequences (GenBank accession number L05144, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human PEPCK-cytosolic mRNA levels by quantitative real-time PCR as described in other examples herein. Data are averages from two experiments. If present, "N.D." indicates "no data".

TABLE 1

Inhibition of human PEPCK-cytosolic mRNA levels by chimeric phosphorothioate oligonucleotides having 2'-MOE wings and a deoxy gap

| ISI # | REGION | TARGET SEQ ID NO | TARGET SITE | SEQUENCE | % INHIB | SEQ ID NO |
|---|---|---|---|---|---|---|
| 108077 | 5'UTR | 3 | 10 | ctcttcccgccagcaagttt | 51 | 18 |
| 108078 | 5'UTR | 3 | 50 | tggatgatctcgaagggaga | 0 | 19 |
| 108032 | Start Codon | 3 | 103 | tttctgcagagtgctgctaa | 64 | 20 |
| 108033 | Start Codon | 3 | 105 | catttctgcagagtgctgct | 15 | 21 |
| 108034 | Start Codon | 3 | 107 | ggcatttctgcagagtgctg | 39 | 22 |
| 108035 | Start Codon | 3 | 109 | gaggcatttctgcagagtgc | 42 | 23 |
| 108036 | Start Codon | 3 | 111 | aggaggcatttctgcagagt | 41 | 24 |
| 108037 | Start Codon | 3 | 113 | tgaggaggcatttctgcaga | 40 | 25 |
| 108038 | Start Codon | 3 | 115 | gctgaggaggcatttctgca | 60 | 26 |
| 108039 | Start Codon | 3 | 117 | cagctgaggaggcatttctg | 29 | 27 |
| 108040 | Start Codon | 3 | 119 | tgcagctgaggaggcatttc | 40 | 28 |
| 108041 | Start Codon | 3 | 121 | tttgcagctgaggaggcatt | 64 | 29 |
| 108042 | Start Codon | 3 | 123 | gttttgcagctgaggaggca | 55 | 30 |
| 108043 | Coding | 3 | 125 | ccgttttgcagctgaggagg | 24 | 31 |
| 108044 | Coding | 3 | 138 | cgagaggttcaggccgtttt | 70 | 32 |
| 108045 | Coding | 3 | 168 | gctgtccaggcttccctgga | 47 | 33 |
| 108046 | Coding | 3 | 220 | gctgacacagctcagcgtta | 54 | 34 |
| 108047 | Coding | 3 | 251 | tcagagccgtcacagatgtg | 46 | 35 |
| 108048 | Coding | 3 | 277 | ggcccagaagccgcccattc | 79 | 36 |
| 108049 | Coding | 3 | 302 | ctgaggatgccctcttcctc | 70 | 37 |
| 108050 | Coding | 3 | 327 | gcagttgtcatacttcttca | 0 | 38 |
| 108051 | Coding | 3 | 371 | ctttcgatcctggccacatc | 57 | 39 |
| 108052 | Coding | 3 | 397 | gctcttgggtgacgataacc | 75 | 40 |
| 108053 | Coding | 3 | 439 | gctggctgaggcctgttttg | 59 | 41 |
| 108054 | Coding | 3 | 465 | atcctcctctgacatccagc | 48 | 42 |
| 108055 | Coding | 3 | 493 | ggaacctggcattgaacgct | 47 | 43 |
| 108056 | Coding | 3 | 523 | cgtacatggtgcgaccttc | 55 | 44 |
| 108057 | Coding | 3 | 549 | cagcggcccatgctgaatg | 32 | 45 |
| 108058 | Coding | 3 | 581 | agctcgatgccgatcttcga | 74 | 46 |
| 108059 | Coding | 3 | 612 | catgctggccaccacgtagg | 75 | 47 |
| 108060 | Coding | 3 | 642 | gacgggcgtgcccatccgcg | 52 | 48 |
| 108061 | Coding | 3 | 674 | ttgacaaactcccatcgcc | 7 | 49 |
| 108062 | Coding | 3 | 709 | gtaaaggcagagggcacccc | 57 | 50 |

TABLE 1-continued

Inhibition of human PEPCK-cytosolic mRNA levels by chimeric phosphorothioate oligonucleotides having 2'-MOE wings and a deoxy gap

| ISI # | REGION | TARGET SEQ ID NO | TARGET SITE | SEQUENCE | % INHIB | SEQ ID NO |
|---|---|---|---|---|---|---|
| 108063 | Coding | 3 | 741 | gttgcagggccagttgttga | 57 | 51 |
| 108064 | Coding | 3 | 774 | gtcaggcaggtgggcgatga | 34 | 52 |
| 108065 | Coding | 3 | 809 | ccgtacccactgccaaagga | 69 | 53 |
| 108066 | Coding | 3 | 841 | caaagcacttcttcccgagc | 58 | 54 |
| 108067 | Coding | 3 | 876 | ttcctcctctgccagccggc | 88 | 55 |
| 108068 | Coding | 3 | 912 | tatacccagaatcagcatgt | 13 | 56 |
| 108069 | Coding | 3 | 946 | ccgccaggtacttcttctca | 75 | 57 |
| 108070 | Coding | 3 | 980 | aggttggtcttcccgcaggc | 56 | 58 |
| 108071 | Coding | 3 | 1045 | tccaggcaatgtcatccccg | 27 | 59 |
| 108072 | Coding | 3 | 1086 | tgggttgatgggcccttaaat | 54 | 60 |
| 108073 | Coding | 3 | 1158 | ctggatggtcttgatggcat | 0 | 61 |
| 108074 | Coding | 3 | 1198 | cgtcgctggtctcggccaca | 70 | 62 |
| 108075 | Coding | 3 | 1254 | cgtgatggtgacgcctgaag | 15 | 63 |
| 108076 | Coding | 3 | 1295 | ggttccccatcctctgagct | 11 | 64 |
| 108079 | Coding | 3 | 1386 | aatgggaacaccttccggag | 26 | 65 |
| 108080 | Coding | 3 | 1427 | gggacaccagcaggtctacg | 6 | 66 |
| 108081 | Coding | 3 | 1467 | aaagactccatgttgccagc | 83 | 67 |
| 108082 | Coding | 3 | 1524 | gattttgcctttatgttctg | 27 | 68 |
| 108083 | Coding | 3 | 1582 | ggtatttgccgaagttgtag | 39 | 69 |
| 108084 | Coding | 3 | 1623 | ttggctgctgggtgctggg | 50 | 70 |
| 108085 | Coding | 3 | 1663 | tgtccttccggaaccagttg | 44 | 71 |
| 108086 | Coding | 3 | 1704 | ggagttctctccaaagcctg | 12 | 72 |
| 108087 | Coding | 3 | 1744 | cttttccatcgatccggttg | 35 | 73 |
| 108088 | Coding | 3 | 1801 | tcaggttcagggcatcctcc | 68 | 74 |
| 108089 | Coding | 3 | 1842 | gatgctgaaaagctccatca | 61 | 75 |
| 108090 | Coding | 3 | 1882 | tctcgatgtcttccacctcc | 58 | 76 |
| 108091 | Coding | 3 | 1939 | ggatctctctctcgatttca | 63 | 77 |
| 108092 | Stop Codon | 3 | 1982 | tcaggccctgattacatctg | 70 | 78 |
| 108093 | 3'UTR | 3 | 2025 | ttaaaggtaaagcactcagg | 53 | 79 |
| 108094 | 3'UTR | 3 | 2058 | ctactgcaccttatggattt | 48 | 80 |
| 108095 | 3'UTR | 3 | 2094 | tggcgtcaatttgggaacac | 53 | 81 |
| 108096 | 3'UTR | 3 | 2123 | ctgctcccggtgtggtgatg | 45 | 82 |
| 108097 | 3'UTR | 3 | 2174 | ccagtgttctgtggttctta | 78 | 83 |
| 108098 | 3'UTR | 3 | 2207 | aagatttcccttctcaattt | 19 | 84 |
| 108099 | 3'UTR | 3 | 2253 | aatttgaacaaagtatgcat | 17 | 85 |
| 108100 | 3'UTR | 3 | 2286 | aacactgaaaagatcaatgc | 32 | 86 |
| 108105 | 3'UTR | 3 | 2353 | atatatatatacagctcaag | 45 | 87 |
| 108106 | 3'UTR | 3 | 2373 | acacacacacacacacacac | 34 | 88 |
| 108107 | 3'UTR | 3 | 2398 | tgtgcacatacatgcacaca | 0 | 89 |
| 108108 | 3'UTR | 3 | 2416 | aaatatcacacagacacatg | 0 | 90 |
| 108109 | 3'UTR | 3 | 2431 | acaaatacacataccaaata | 16 | 91 |
| 108110 | 3'UTR | 3 | 2451 | tattttgaataacagtacat | 0 | 92 |
| 108111 | 3'UTR | 3 | 2466 | caaaggtattaaatatattt | 0 | 93 |
| 108101 | 3'UTR | 3 | 2488 | ggtcatcttgcccaagattt | 78 | 94 |
| 108102 | 3'UTR | 3 | 2502 | aaggaaaactagtaggtcat | 32 | 95 |
| 108103 | 3'UTR | 3 | 2538 | ttaagcacaatattaataac | 8 | 96 |
| 108104 | 3'UTR | 3 | 2573 | tgtaaaggtaaggaacaatg | 21 | 97 |

As shown in Table 1, SEQ ID NOs 18, 20, 22, 23, 24, 25, 26, 27, 28, 29, 30, 32, 33, 34, 35, 36, 37, 39, 40, 41, 42, 43, 44, 45, 46, 47, 48, 50, 51, 52, 53, 54, 55, 57, 58, 59, 60, 62, 65, 67, 68, 69, 70, 71, 73, 74, 75, 76, 77, 78, 79, 80, 81, 82, 83, 86, 87, 88, 94 and 95 demonstrated at least 25% inhibition of human PEPCK-cytosolic expression in this assay and are therefore preferred.

Example 17
Antisense inhibition of mouse PEPCK-cytosolic expression by chimeric phosphorothioate oligonucleotides having 2'-MOE wings and a deoxy gap.

In accordance with the present invention, a second series of oligonucleotides were designed to target different regions of the mouse PEPCK-cytosolic RNA, using published sequences (GenBank accession number AF009605, incorporated herein as SEQ ID NO: 10), and a cDNA sequence derived from the AF009605 genomic sequence using the GenBank "feature" function and incorporated herein as SEQ ID NO: 17. series of oligonucleotides were designed to target different regions of the mouse PEPCK-cytosolic RNA, using published sequences (GenBank accession number AF009605, incorporated herein as SEQ ID NO: 10, and GenBank accession number AF009605, a genomic sequence from which the cDNA was derived and is incorporated herein as SEQ ID NO: 17). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are comppposed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse PEPCK-cytosolic mRNA levels by quantitative real-time PCR as described in other examples herein. Data are averages from two experiments. If present, "N.D." indicates "no data".

TABLE 2

Inhibition of mouse PEPCK-cytosolic mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 113362 | 5'UTR | 10 | 5588 | ccctgcctacctttcttcct | 0 | 98 |
| 113336 | 5'UTR | 10 | 5616 | tgtatttttggagaggtgaa | 0 | 99 |
| 113346 | 5'UTR | 10 | 5639 | aagaacatgagtgggcccct | 0 | 100 |
| 113340 | 5'UTR | 10 | 5651 | ggaaaaccttccaagaacat | 0 | 101 |
| 113330 | 5'UTR | 10 | 5681 | cacttactttactgggacgg | 0 | 102 |
| 113351 | 5'UTR | 10 | 5724 | gggtattcttgtactcaccc | 0 | 103 |
| 113333 | Intron | 10 | 6208 | ctcttaagcttctcaggtgt | 0 | 104 |
| 113341 | Intron | 10 | 6319 | ggagcttgaccaggtggaca | 0 | 105 |
| 113347 | Intron | 10 | 6414 | aagtcacagggactccttca | 7 | 106 |
| 113339 | Intron | 10 | 6690 | tgggccacgctttgcagctc | 0 | 107 |
| 113352 | Intron | 10 | 6720 | gaaacagaaccagacagtgc | 31 | 108 |
| 113338 | Intron | 10 | 6862 | tttcttttgagaccaagtgt | 25 | 109 |
| 113344 | Intron | 10 | 6999 | aggcagcttaacatccacat | 38 | 110 |
| 113334 | Intron | 10 | 7039 | tgcaaagtgctgaaattaaa | 0 | 111 |
| 113354 | Intron | 10 | 7083 | tgcctttggccacgaacct | 22 | 112 |
| 113353 | Intron | 10 | 7087 | atcatgcctttggccacga | 26 | 113 |
| 113337 | Intron | 10 | 7487 | caaactcagggcctcatgca | 45 | 114 |
| 113357 | Intron | 10 | 7532 | tggtaggcctgacccagcat | 0 | 115 |
| 113363 | Coding | 10 | 7672 | accaaaggctctgcaaacaa | 0 | 116 |
| 113331 | Intron | 10 | 8118 | agggtcttcccaaaggcaga | 6 | 117 |
| 113349 | Intron | 10 | 8416 | atggacgggatcagctttag | 0 | 118 |
| 113360 | Coding | 10 | 8597 | gaagactcaccttgggcatc | 0 | 119 |
| 113342 | Intron | 10 | 9083 | gtgtgtgtgagtgtgtgtga | 0 | 120 |
| 113358 | Intron | 10 | 9237 | actctgcagttttctgcttc | 29 | 121 |
| 113345 | Intron | 10 | 9324 | ctagctcatgtcctaaagtt | 0 | 122 |
| 113350 | Intron | 10 | 9358 | caagcatcccagagttctta | 22 | 123 |
| 113356 | Intron | 10 | 9373 | ggtatgaatgcaagccaagc | 0 | 124 |
| 113359 | Intron | 10 | 9382 | agagaaggaggtatgaatgc | 37 | 125 |
| 113355 | Intron | 10 | 9655 | agccagagcacacagcctct | 0 | 126 |
| 113332 | Intron | 10 | 9701 | acgagagagataccccttag | 4 | 127 |
| 113361 | Coding | 10 | 9725 | catggttccgctgcaagaga | 0 | 128 |
| 113364 | Coding | 10 | 9857 | gatgcctcaccttcaggtct | 0 | 129 |
| 113343 | Intron | 10 | 9938 | agatcctttggaaccagctt | 0 | 130 |
| 113335 | Intron | 10 | 10133 | agttttctgttgtgagttaacc | 0 | 131 |
| 113348 | Intron | 10 | 10365 | ttccttccttccttcctcct | 0 | 132 |
| 113365 | 3'UTR | 10 | 11752 | ataaaagtttattttgtaat | 0 | 133 |
| 113366 | 3'UTR | 10 | 11754 | ctataaaagtttattttgta | 0 | 134 |
| 113305 | 5'UTR | 17 | 7 | gtgttcccagagggaaggcc | 0 | 135 |
| 113312 | 5'UTR | 17 | 44 | tgagcgccttgccggatttc | 0 | 136 |
| 113327 | 5'UTR | 17 | 90 | ctggtgccacctttcttcct | 0 | 137 |
| 113318 | 5'UTR | 17 | 119 | ttgcaatggtgtggagagag | 0 | 138 |
| 113289 | Start Codon | 17 | 125 | gcataattgcaatggtgtgg | 0 | 139 |
| 113367 | Start Codon | 17 | 133 | ctgaggaggcataattgcaa | 30 | 140 |
| 113311 | Coding | 17 | 257 | agatgtggatatactccggc | 0 | 141 |
| 113313 | Coding | 17 | 318 | atgacaccctcctcctgcat | 0 | 142 |
| 113326 | Coding | 17 | 355 | agccagccaacagttgtcat | 0 | 143 |
| 113296 | Coding | 17 | 413 | cttgggtgatgatgactgtc | 0 | 144 |
| 113303 | Coding | 17 | 421 | tctctgctcttgggtgatga | 29 | 145 |
| 113315 | Coding | 17 | 461 | ccagctggctgaggccagtt | 0 | 146 |
| 113306 | Coding | 17 | 493 | ttttctcaaagtcctcttccg | 0 | 147 |
| 113319 | Coding | 17 | 519 | caccctgggaacctggcgtt | 14 | 148 |
| 113328 | Coding | 17 | 537 | atggtgcggcctttcatgca | 0 | 149 |
| 113307 | Coding | 17 | 554 | tgaatgggatgacatacatg | 10 | 150 |
| 113302 | Coding | 17 | 557 | tgctgaatgggatgacatac | 0 | 151 |
| 113299 | Coding | 17 | 892 | ctccttagccagacggctgg | 0 | 152 |
| 113325 | Coding | 17 | 1092 | cttaagttgccttgggcatc | 11 | 153 |
| 113295 | Coding | 17 | 1119 | aaaaaccccgttttctgggtt | 0 | 154 |
| 113292 | Coding | 17 | 1159 | atttggatttgtcttcactg | 0 | 155 |
| 113321 | Coding | 17 | 1210 | agtctcggccacgttggtga | 0 | 156 |
| 113304 | Coding | 17 | 1226 | aaacaccccccatcgctagtc | 27 | 157 |
| 113316 | Coding | 17 | 1244 | catcgatgccttcccagtaa | 0 | 158 |
| 113301 | Coding | 17 | 1421 | caaagatgataccctcaatg | 0 | 159 |
| 113297 | Coding | 17 | 1527 | tctgcagcagctgtggcctc | 0 | 160 |
| 113329 | Coding | 17 | 1545 | atgatcttgccccttgtgttc | 0 | 161 |
| 113324 | Coding | 17 | 1600 | gtatttgccgaagttgtagc | 23 | 162 |

TABLE 2-continued

Inhibition of mouse PEPCK-cytosolic mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 113291 | Coding | 17 | 1624 | ggccatgctcagccagtggg | 0 | 163 |
| 113294 | Coding | 17 | 1702 | ccagaggaacttgccatctt | 0 | 164 |
| 113323 | Coding | 17 | 1751 | tccgcccgaacatccactcc | 0 | 165 |
| 113308 | Coding | 17 | 1792 | gtagccgatgggcgtgagct | 0 | 166 |
| 113298 | Coding | 17 | 1947 | tcaatttcgtaagggaggtc | 0 | 167 |
| 113290 | Coding | 17 | 1978 | gattctctgtttcagggctc | 0 | 168 |
| 113368 | Stop Codon | 17 | 1998 | attgggatttacatctggct | 35 | 169 |
| 113314 | 3'UTR | 17 | 2117 | aaaggtgctttctgatcta | 15 | 170 |
| 113317 | 3'UTR | 17 | 2122 | tattaaaaggtgcttttctg | 0 | 171 |
| 113310 | 3'UTR | 17 | 2231 | tggaaccaaaacccccattg | 0 | 172 |
| 113300 | 3'UTR | 17 | 2298 | ttttctgtgcattttagcta | 53 | 173 |
| 113309 | 3'UTR | 17 | 2309 | gctcaagtatgttttctgtg | 37 | 174 |
| 113322 | 3'UTR | 17 | 2349 | cacatgctcacacagagaca | 0 | 175 |
| 113293 | 3'UTR | 17 | 2464 | tacaaatttgcccaagattt | 45 | 176 |
| 113320 | 3'UTR | 17 | 2510 | aaacatacatactagcaaca | 9 | 177 |

As shown in Table 2, SEQ ID NOs 108, 110, 113, 114, 121, 125, 140, 145, 157, 169, 173, 174 and 176 demonstrated at least 25% inhibition of mouse PEPCK-cytosolic expression in this experiment and are therefore preferred.

Example 18
Western blot analysis of PEPCK-cytosolic protein levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to PEPCK-cytosolic is used, with a radiolabelled or fluorescently labeled secondary antibody directed against the primary antibody species. Bands are visualized using a PHOSPHORIMAGERT (Molecular Dynamics, Sunnyvale Calif.).

What is claimed is:

1. An antisense compound up to 30 nucleobases in length comprising at least an 8-nucleobase portion of SEQ ID NO: 18, 20, 22, 23, 24, 25, 26, 27, 28, 29, 30, 32, 33, 34, 35, 36, 37, 39, 40, 41, 42, 43, 44, 45, 46, 47, 48, 50, 51, 52, 53, 54, 55, 57, 58, 59, 60, 62, 65, 67, 68, 69, 70, 71, 73, 74, 75, 76, 77, 78, 79, 80, 81, 82, 83, 86, 87, 88, 94, 95, 108, 110, 113, 114, 121, 125, 140, 145, 157, 169, 173, 174 or 176 which inhibits the expression of PEPCK-cytosolic.

2. The antisense compound of claim 1 which is an antisense oligonucleotide.

3. The antisense compound of claim 2 wherein the antisense oligonucleotide comprises at least one modified internucleoside linkage.

4. The antisense compound of claim 3 wherein the modified internucleoside linkage is a phosphorothioate linkage.

5. The antisense compound of claim 2 wherein the antisense oligonucleotide comprises at least one modified sugar moiety.

6. The antisense compound of claim 5 wherein the modified sugar moiety is a 2'-O-methoxyethyl sugar moiety.

7. The antisense compound of claim 2 wherein the antisense oligonucleotide comprises at least one modified nucleobase.

8. The antisense compound of claim 7 wherein the modified nucleobase is a 5-methylcytosine.

9. The antisense compound of claim 2 wherein the antisense oligonucleotide is a chimeric oligonucleotide.

10. A method of inhibiting the expression of PEPCK-cytosolic in cells or tissues comprising contacting said cells or tissues in vitro with the antisense compound of claim 1 so that expression of PEPCK-cytosolic is inhibited.

* * * * *

SEQUENCE LISTING

```
<160> NUMBER OF SEQ ID NOS: 177

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                          20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                          20

<210> SEQ ID NO 3
<211> LENGTH: 2657
<212> TYPE: DNA
<213> ORGANISM: Homo sapiens
<220> FEATURE:
<221> NAME/KEY: CDS
<222> LOCATION: (122)...(1990)
```

-continued

```
<400> SEQUENCE: 3
tgggaacaca aacttgctgg cgggaagagc ccggaaagaa acctgtggat ctcccttcga      60
gatcatccaa agagaagaaa ggtgacctca cattcgtgcc ccttagcagc actctgcaga     120 a atg cct cct cag ctg caa aac ggc ctg aac ctc tcg gcc aaa gtt gtc    169
  Met Pro Pro Gln Leu Gln Asn Gly Leu Asn Leu Ser Ala Lys Val Val
   1               5                  10                  15 cag gga agc ctg gac agc ctg ccc cag gca gtg agg gag ttt ctc gag      217
Gln Gly Ser Leu Asp Ser Leu Pro Gln Ala Val Arg Glu Phe Leu Glu
             20                  25                  30 aat aac gct gag ctg tgt cag cct gat cac atc cac atc tgt gac ggc      265
Asn Asn Ala Glu Leu Cys Gln Pro Asp His Ile His Ile Cys Asp Gly
         35                  40                  45 tct gag gag gag aat ggg cgg ctt ctg ggc cag atg gag gaa gag ggc      313
Ser Glu Glu Glu Asn Gly Arg Leu Leu Gly Gln Met Glu Glu Glu Gly
     50                  55                  60 atc ctc agg cgg ctg aag aag tat gac aac tgc tgg ttg gct ctc act      361
Ile Leu Arg Arg Leu Lys Lys Tyr Asp Asn Cys Trp Leu Ala Leu Thr
 65                  70                  75                  80 gac ccc agg gat gtg gcc agg atc gaa agc aag acg gtt atc gtc acc      409
Asp Pro Arg Asp Val Ala Arg Ile Glu Ser Lys Thr Val Ile Val Thr
                 85                  90                  95 caa gag caa aga gac aca gtg ccc atc ccc aaa aca ggc ctc agc cag      457
Gln Glu Gln Arg Asp Thr Val Pro Ile Pro Lys Thr Gly Leu Ser Gln
            100                 105                 110 ctc ggt cgc tgg atg tca gag gag gat ttt gag aaa gcg ttc aat gcc      505
Leu Gly Arg Trp Met Ser Glu Glu Asp Phe Glu Lys Ala Phe Asn Ala
        115                 120                 125 agg ttc cca ggg tgc atg aaa ggt cgc acc atg tac gtc atc cca ttc      553
Arg Phe Pro Gly Cys Met Lys Gly Arg Thr Met Tyr Val Ile Pro Phe
    130                 135                 140 agc atg ggg ccg ctg ggc tca cct ctg tcg aag atc ggc atc gag ctg      601
Ser Met Gly Pro Leu Gly Ser Pro Leu Ser Lys Ile Gly Ile Glu Leu
145                 150                 155                 160 acg gat tcg ccc tac gtg gtg gcc agc atg cgg atc atg acg cgg atg      649
Thr Asp Ser Pro Tyr Val Val Ala Ser Met Arg Ile Met Thr Arg Met
                165                 170                 175 ggc acg ccc gtc ctg gaa gca ctg ggc gat ggg gag ttt gtc aaa tgc      697
Gly Thr Pro Val Leu Glu Ala Leu Gly Asp Gly Glu Phe Val Lys Cys
            180                 185                 190 ctc cat tct gtg ggg tgc cct ctg cct tta caa aag cct ttg gtc aac      745
Leu His Ser Val Gly Cys Pro Leu Pro Leu Gln Lys Pro Leu Val Asn
        195                 200                 205 aac tgg ccc tgc aac ccg gag ctg acg ctc atc gcc cac ctg cct gac      793
Asn Trp Pro Cys Asn Pro Glu Leu Thr Leu Ile Ala His Leu Pro Asp
    210                 215                 220 cgc aga gag atc atc tcc ttt ggc agt ggg tac ggc ggg aac tcg ctg      841
Arg Arg Glu Ile Ile Ser Phe Gly Ser Gly Tyr Gly Gly Asn Ser Leu
225                 230                 235                 240 ctc ggg aag aag tgc ttt gct ctc agg atg gcc agc cgg ctg gca gag      889
Leu Gly Lys Lys Cys Phe Ala Leu Arg Met Ala Ser Arg Leu Ala Glu
                245                 250                 255 gag gaa ggg tgg ctg gca gag cac atg ctg att ctg ggt ata acc aac      937
Glu Glu Gly Trp Leu Ala Glu His Met Leu Ile Leu Gly Ile Thr Asn
            260                 265                 270 cct gag ggt gag aag aag tac ctg gcg gcc gca ttt ccc agc gcc tgc      985
Pro Glu Gly Glu Lys Lys Tyr Leu Ala Ala Ala Phe Pro Ser Ala Cys
        275                 280                 285
```

-continued

| | |
|---|---|
| ggg aag acc aac ctg gcc atg atg aac ccc agc ctc ccc ggg tgg aag<br>Gly Lys Thr Asn Leu Ala Met Met Asn Pro Ser Leu Pro Gly Trp Lys<br>290                                      295                             300 | 1033 |
| gtt gag tgc gtc ggg gat gac att gcc tgg atg aag ttt gac gca caa<br>Val Glu Cys Val Gly Asp Asp Ile Ala Trp Met Lys Phe Asp Ala Gln<br>305                                   310                         315                      320 | 1081 |
| ggt cat tta agg gcc atc aac cca gaa aat ggc ttt ttc ggt gtc gct<br>Gly His Leu Arg Ala Ile Asn Pro Glu Asn Gly Phe Phe Gly Val Ala<br>                            325                         330                          335 | 1129 |
| cct ggg act tca gtg aag acc aac ccc aat gcc atc aag acc atc cag<br>Pro Gly Thr Ser Val Lys Thr Asn Pro Asn Ala Ile Lys Thr Ile Gln<br>                   340                         345                         350 | 1177 |
| aag aac aca atc ttt acc aat gtg gcc gag acc agc gac ggg ggc gtt<br>Lys Asn Thr Ile Phe Thr Asn Val Ala Glu Thr Ser Asp Gly Gly Val<br>                            355                         360                        365 | 1225 |
| tac tgg gaa ggc att gat gag ccg cta gct tca ggc gtc acc atc acg<br>Tyr Trp Glu Gly Ile Asp Glu Pro Leu Ala Ser Gly Val Thr Ile Thr<br>370                                      375                         380 | 1273 |
| tcc tgg aag aat aag gag tgg agc tca gag gat ggg gaa cct tgt gcc<br>Ser Trp Lys Asn Lys Glu Trp Ser Ser Glu Asp Gly Glu Pro Cys Ala<br>385                                    390                         395                      400 | 1321 |
| cac ccc aac tcg agg ttc tgc acc cct gcc agc cag tgc ccc atc att<br>His Pro Asn Ser Arg Phe Cys Thr Pro Ala Ser Gln Cys Pro Ile Ile<br>                            405                         410                        415 | 1369 |
| gat gct gcc tgg gag tct ccg gaa ggt gtt ccc att gaa ggc att atc<br>Asp Ala Ala Trp Glu Ser Pro Glu Gly Val Pro Ile Glu Gly Ile Ile<br>                   420                         425                         430 | 1417 |
| ttt gga ggc cgt aga cct gct ggt gtc cct cta gtc tat gaa gct ctc<br>Phe Gly Gly Arg Arg Pro Ala Gly Val Pro Leu Val Tyr Glu Ala Leu<br>                            435                         440                        445 | 1465 |
| agc tgg caa cat gga gtc ttt gtg ggg gcg gcc atg aga tca gag gcc<br>Ser Trp Gln His Gly Val Phe Val Gly Ala Ala Met Arg Ser Glu Ala<br>450                                      455                         460 | 1513 |
| aca gcg gct gca gaa cat aaa ggc aaa atc atc atg cat gac ccc ttt<br>Thr Ala Ala Ala Glu His Lys Gly Lys Ile Ile Met His Asp Pro Phe<br>465                                    470                         475                      480 | 1561 |
| gcc atg cgg ccc ttc ttt ggc tac aac ttc ggc aaa tac ctg gcc cac<br>Ala Met Arg Pro Phe Phe Gly Tyr Asn Phe Gly Lys Tyr Leu Ala His<br>                            485                         490                        495 | 1609 |
| tgg ctt agc atg gcc cag cac cca gca gcc aaa ctg ccc aag atc ttc<br>Trp Leu Ser Met Ala Gln His Pro Ala Ala Lys Leu Pro Lys Ile Phe<br>                   500                         505                         510 | 1657 |
| cat gtc aac tgg ttc cgg aag gac aag gaa ggc aaa ttc ctc tgg cca<br>His Val Asn Trp Phe Arg Lys Asp Lys Glu Gly Lys Phe Leu Trp Pro<br>                            515                         520                        525 | 1705 |
| ggc ttt gga gag aac tcc agg gtg ctg gag tgg atg ttc aac cgg atc<br>Gly Phe Gly Glu Asn Ser Arg Val Leu Glu Trp Met Phe Asn Arg Ile<br>530                                    535                         540 | 1753 |
| gat gga aaa gcc agc acc aac gtc acg ccc ata ggc tac atc ccc aag<br>Asp Gly Lys Ala Ser Thr Asn Val Thr Pro Ile Gly Tyr Ile Pro Lys<br>545                                    550                         555                      560 | 1801 |
| gag gat gcc ctg aac ctg aaa ggc ctg ggg cac atc aac atg atg gag<br>Glu Asp Ala Leu Asn Leu Lys Gly Leu Gly His Ile Asn Met Met Glu<br>                   565                         570                         575 | 1849 |
| ctt ttc agc atc tcc aag gaa ttc tgg gac aag gag gtg gaa gac atc<br>Leu Phe Ser Ile Ser Lys Glu Phe Trp Asp Lys Glu Val Glu Asp Ile<br>                            580                         585                        590 | 1897 |
| gag aag tat ctg gtg gat caa gtc aat gcc gac ctc ccc tgt gaa atc<br>Glu Lys Tyr Leu Val Asp Gln Val Asn Ala Asp Leu Pro Cys Glu Ile<br>                            595                         600                      605 | 1945 |

-continued

| | |
|---|---|
| gag aga gag atc ctt gcc ttg aag caa aga ata agc cag atg taa<br>Glu Arg Glu Ile Leu Ala Leu Lys Gln Arg Ile Ser Gln Met<br>  610                615                620 | 1990 |
| tcagggcctg agaataagcc agatgtaatc agggcctgag tgctttacct ttaaaatcat | 2050 |
| taaattaaaa tccataaggt gcagtaggag caagagaggg caagtgttcc caaattgacg | 2110 |
| ccacctaata atcatcacca caccgggagc agatctgaag gcacactttg atttttttaa | 2170 |
| ggataagaac cacagaacac tgggtagtag ctaatgaaat tgagaaggga atcttagca | 2230 |
| tgcctccaaa aattcacatc caatgcatac tttgttcaaa tttaaggtta ctcaggcatt | 2290 |
| gatcttttca gtgtttttc acttagctat gtggattagc tagaatgcac accaaaaaga | 2350 |
| tacttgagct gtatatatat atgtgtgtgt gtgtgtgtgt gtgtgtgtgt gtgcatgtat | 2410 |
| gtgcacatgt gtctgtgtga tatttggtat gtgtatttgt atgtactgtt attcaaaata | 2470 |
| tatttaatac ctttggaaaa tcttgggcaa gatgacctac tagttttcct tgaaaaaaag | 2530 |
| ttgctttgtt attaatattg tgcttaaatt attttatac accattgttc cttacctttta | 2590 |
| cataattgca atatttcccc cttactactt cttggaaaaa aattagaaaa tgaagtttat | 2650 |
| agaaaag | 2657 |

<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4
tgggctcacc tctgtcgaa                    19

<210> SEQ ID NO 5
<211> LENGTH: 16
<212> TYPE: DNA
<213> ORGANISM: Artificial Sequence
<220> FEATURE:
<223> OTHER INFORMATION: PCR Primer

<400> SEQUENCE: 5
tgcccatccg cgtcat                       16

<210> SEQ ID NO 6
<211> LENGTH: 24
<212> TYPE: DNA
<213> ORGANISM: Artificial Sequence
<220> FEATURE:
<223> OTHER INFORMATION: PCR Probe

<400> SEQUENCE: 6
ctgacggatt cgccctacgt ggtg              24

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                    19

```
<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                              20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                              20

<210> SEQ ID NO 10
<211> LENGTH: 12141
<212> TYPE: DNA
<213> ORGANISM: Mus musculus
<220> FEATURE:
<221> NAME/KEY: CDS
<222> LOCATION: (5895)...(6118)
<220> FEATURE:
<221> NAME/KEY: CDS
<222> LOCATION: (6440)...(6621)
<220> FEATURE:
<221> NAME/KEY: CDS
<222> LOCATION: (7206)...(7409)
<220> FEATURE:
<221> NAME/KEY: CDS
<222> LOCATION: (7682)...(7869)
<220> FEATURE:
<221> NAME/KEY: CDS
<222> LOCATION: (8444)...(8606)
<220> FEATURE:
<221> NAME/KEY: CDS
<222> LOCATION: (9418)...(9642)
<220> FEATURE:
<221> NAME/KEY: CDS
<222> LOCATION: (9735)...(9866)
<220> FEATURE:
<221> NAME/KEY: CDS
<222> LOCATION: (10502)...(10597)
<220> FEATURE:
<221> NAME/KEY: CDS
<222> LOCATION: (10701)...(11155)

<400> SEQUENCE: 10
tccaccggga gacccatga  agtccacggt gtttctcacg atttcctggt ccgtagactc    60
tgtcctgggc caccacccat ctttctctca aacccttgc  atcttgatgg ggcctggcca   120
gggttagatt gctttttttc tggaggcagg gtcttgtgtt gctgtgtctg gtcttgaatg   180
tattatgtag ccaaggatga ccttggacac tttaatcctc ctgttttcac ctcctggatt   240
gctagggatt gcaggtgttt accaccatgt ctgattcatg ggggtctggg gatcaaaccc   300
agggctttgt gcatgcggcc ttcatcttgc ttcctaactg ctctattctg tatgggcttc   360
tagagccctg aagacagcct gtctgaagaa accatcaggc tgatgtatta cccagcactc   420
tttatctcta cctggctcag gaggtcagca acatcaggag gcgcaagagc ctggctggga   480
ggctcggagt ccttggcttt aaaagattcc ttaaatgtat gctcagccgt gtctgtttgt   540
ctcgtggctt ctgaggacaa gtgtaagcat gtctgggaag gtacttgtga ccgtaggacc   600
cacagtttct gtctacgtca tcactattga tcctagtttg tatgcaaata cagctatcaa   660
```

-continued

| | |
|---|---|
| tgttgtcctc acaggacatg agctgtggac atggggatgg ggcaggtgtg tgtagcctct | 720 |
| ttttctatag gaccactgag tgagtcaaac tcactatcct cctgcctctg cctcctggat | 780 |
| ccatgtatgg attatactgt acatggcagg ataatctatc tatctatcta tctatctatc | 840 |
| tatctatcta tctatctatc tatctaatta actctattgc tatctctctt ttgcttttt | 900 |
| gagacaggtt ttctctgtat agccctggct gtcctggaac tcactctgta aaccaggctg | 960 |
| gctcgaactc acagaaatcc acctgcctcc gcctcctgag tgcttaaaag catagctaaa | 1020 |
| ggtgtgctcc accaccaccc agctcaggaa ttttcttaga gcattcagca ccacatgtat | 1080 |
| gggctggctg tgtgattagc caagtacaga acaaaaaaaa atgaagaacc cttggttcta | 1140 |
| aaaggatgac gagacatttc tcttttctt agctttctcc acctgcatgg tgcccacaac | 1200 |
| ttgatagtta aaggtcacac tttctcaggc accagaatac tgacagacat cagaagatgc | 1260 |
| ctgaagatgc ctggacccaa ccaaactccc tctgctgagg cacaggtcct tttcagggtc | 1320 |
| gtctactggg aagggtggtc acaaaggccc aggaacagag aatatattct tccaagagcc | 1380 |
| agccatgcgc atagcttctt gcgtcgtcct ggggatgagt atgcatgtgg tgtcggctgt | 1440 |
| gtgtctgaca gtgaagtcct agagtcatac agagctgata aaagccctag gctcaaagtc | 1500 |
| tgtggaactt ttattctgct caagaatacc agtagccatc cagccagtgt ttgctgagtg | 1560 |
| aacgcatgtg attcctttct cgagcctcaa tttcctgatc tctaaattgg agaaggacaa | 1620 |
| tgacgatcgg agaggaccat gggaagcccg cctttaggaa gtttgttctt cacagggctg | 1680 |
| ggacccagag ggcactggag agagtgcagt taacaaatgg gactttaaat agttcttat | 1740 |
| cttgtcactc aaggatacaa ccgatgagac tatcgttgag gtaacatgta gagtaggttc | 1800 |
| aggaaggaat catggaagaa gacggctttg atggctgttc ttggttgtca cccttactac | 1860 |
| actaggaatg gactgcaatc cagaaaggga gggcacaccc gggagagatg tttttgcttg | 1920 |
| gtttgaagtg ggtgaatcca cttctagtgt ggatctttga ggtaggaaga cacaaaccac | 1980 |
| aaactctttt tggttttct ttgttttgct tttctgagac acagtttctt tgtatagccc | 2040 |
| tggctgtcct gaaactggct ttgtataacc aactggccct aactcacaga ggctctgcct | 2100 |
| gcctctgcct cctgagcgtt gggagacaca catcttattc cagatcttga agcaggaatt | 2160 |
| cacaccttta atctgggcca caccttgtgc tggaagtcta tagagggaca cggaagaagg | 2220 |
| aagcttttgc tctctgcctg atgccctccc gatgccaaca catccattcc ttcactgaca | 2280 |
| ttagcaccta attcttcagg attccagcat acacagagga tcagcagaga cagtcagcct | 2340 |
| tgtgggccga gcaactactg gattcttgga cttttcattc acagccagac attgttgcat | 2400 |
| tagctggact gcagcctgta aatcattcca aagagtctct ctctctctct ctctctctct | 2460 |
| ctctctcttt ctctctctct ctctgtgtgt ctctctctct gcctctctct ctatatatat | 2520 |
| aaatatatgt gtgtgtatgt gtatgtgaaa ccatacatat acacatatac atacataaaa | 2580 |
| catattcata tattaacaca cacatatata acacaaacag atagatgata gatagataga | 2640 |
| tagatagata gatgatagat agatagatag atagatagat agatagatag atgatagata | 2700 |
| gatgataggt agatagatag gttgatagat agatgataga tagatagatg atagatagat | 2760 |
| agataggtag atagatagat gggtagatag atagatagat agatagatag atagatgata | 2820 |
| gatagatagg tagatagaaa ggtagataga tagatagatg atagatagat agatgataga | 2880 |
| tagatagata gatagataga tagatagata gatgatagat agatgatgata | 2940 |
| gatgatagat agatagatga tagatagata gatagataga tgatagatag atgatagata | 3000 |
| gatagataga tagatagata gatgatagata tagatagata gatagataga tagacagaca | 3060 |

```
gaccatatgt tctgatactc tagagaacct tgactaatac agcagtataa ttttgagtct   3120
gtttctgagt gtctggcctt cctctcttcc tctttaaagc agctttacat ctggaagcaa   3180
ctgtttacag acttgacaga aagccacttt gacttaaggg aacatgagtt taaggaaccc   3240
ctgagagttt aggggcctc catatgtctg tgtgagaaac cacatgggaa actcccaccc    3300
tgtgggaacc catggccttg tgcctgtcct gtacaagcac tgaacgtcac ataaggtggg   3360
ctgggcactt tctgggacgc ccccagcagg gcagtggcaa ccaacaccca gcagtccctt   3420
tgagacttct tcaagatgaa gcagtaggaa gatgccgtgg ctcacagtgc ctccctggg    3480 aaggggacag agggctgccc agtgaggctt cttgcgggca agaaatcacc aaagacaagg   3540
gaagaccgga cctcaagatg tcctcagtta ggggtgagga cacgctagcc agctttgcct   3600
gactgtcctc agaatcctgc tgtatgtctc agttctccta gaggatcatg gaccccagg    3660 tcattttgaa acccagtttt gacaagatcc agcatagtgt atgtggggat ttggactaat   3720
tggaaggtcg tggggacccc tgctcctcca ccatcattgg gctactatat ccctcccagg   3780
aggcccacag cagaggtacc ttggatgtat gtagagtgat taaaactcca gctgaattaa   3840
tagtctctcc ttttttttc ccaacttaac cttccagggt taagttgaaa caaacggcag    3900
ttttagcagt ggagtggaga ctggccaaga ctctcagagg aagtgtgcac tggaaaggct   3960
ggtttagccc gtgcctgata tggagacact gagcaggaca ctctggctgg gttgacagcc   4020
tatagtttac ataggtgag gccacccttc atgagcagtc tcagtgacct gaagaggaag    4080
ccacttcttc tgtaccgaca cggaaggtcc agtggacgga cccccagaat gctggcagtt   4140
ggggtgcagg aggcattatc tcttcacaca gctttgcaga gtgagtcaag cccccatagt   4200
tcaggccaaa agcactctgt ttgggatggc tctcacagtg cctcaaatct gacacaagtc   4260
ttagtaagca gaagtcacaa agttgcctgt caccatcctc ctgcctacag ggaagtgggc   4320
catgtctctg ccccttactc tgaggccagc tgtgggagcc gggcctgccc atgggctctc   4380
tcccattgac ttctcactca cttctgaact ccgacaagca agctctcagc tcgctcaatt   4440
ggcatgaagg tctgtggcta cgcagagaag tcttacaac tgtggtaaag gtcttgttgc    4500
tcaagtgcca cccagcagca cggccaagcc ccctcccgtc cttctccag acacttgggc    4560 attcaagacg attccaggca gctccaaggg tgatggtgtc taacgcagaa cttcttgaag   4620
aagacactga agggtctaca acagacagca gtcctcccaa gggaccccac agtcctctgt   4680
agcccagcct gcctgatgaa tactcttctg gctctcgcca gccggctggg acctgtttag   4740 tgaccttct gcctcagttt cctggtctgt acccgggatc atcagagatt ccatttcaag    4800
aggtagtaat gaatgatatg acagaaaaca tttagagcag gggtcagtat gtacgtatga   4860
gtgattactg tgagtcaggt attgtcctgt cagaacaaag cttacagcca ctcctaatct   4920
ctgcagtgtt catcttggga tggccagaga atccaccaca cacctagtga ggtaacacac   4980
cccagctaac tcagcaggta cagacattat ctagaagtct catggctcag agctgaattt   5040
ccttctcatg acctttggcc gtgggagtga cacctcacag ctgtggtgtt ttgacaacca   5100
gcagccaccg gcacacaaaa tgtgcagcca gcaacatatg aagtccaaga ggcgtctcgg   5160
ctaggcctgc ccttgacccc cacctgacaa ttaaggcaag agcctgcagt ttgcatcagc   5220
aacaggcagg gtcaaagttt agtcaatcaa atgttgtgta aggactcact atggctgata   5280
gaggggcctg aggcctccca acattcatta acaaccacaa gttcaatcat tatctccctg   5340
gagtttattg tgttaagtca gttccaaacc gtgctgacca tggctatgat ccaaaggcct   5400
gccccttacg tcagaggcga gcctccgggt ccagctgagg ggcagggctg tcctcccttc   5460
```

```
tatatagtat ttaaagcaag gagggcgggc taccaagcac agttggcctt ccctctggga    5520
acacaccctc ggtcaacagg ggaaatccgg caaggcgctc agcgatctct gatccagacc    5580
ttccaaaagg aagaaggta ggcagggtca tttcattcac ctctccaaaa atacaatgag     5640
gggcccactc atgttcttgg aaggttttcc ttctttccat ccgtcccagt aaagtaagtg    5700
gagaggtttt tatgttactc cccgggtgag tacaagaata ccctgacagc catggctccc    5760
tagccacttg caacccatgc aaagtctacg gaaggaccga gaaggggccc atgggtgctc    5820
catggtgttc atgagtccct ttttctgttt caggtggcac cagagttcct gcctctctcc    5880
acaccattgc aatt atg cct cct cag ctg cat aac ggt ctg gac ttc tct      5930
            Met Pro Pro Gln Leu His Asn Gly Leu Asp Phe Ser
              1               5                  10 gcc aag gtt atc cag ggc agc ctc gac agc ctg ccc cag gca gtg agg      5978
Ala Lys Val Ile Gln Gly Ser Leu Asp Ser Leu Pro Gln Ala Val Arg
        15                  20                  25 aag ttc gtg gaa ggc aat gct cag ctg tgc cag ccg gag tat atc cac      6026
Lys Phe Val Glu Gly Asn Ala Gln Leu Cys Gln Pro Glu Tyr Ile His
    30                  35                  40 atc tgc gat ggc tcc gag gag gag tac ggg cag ttg ctg gcc cac atg      6074
Ile Cys Asp Gly Ser Glu Glu Glu Tyr Gly Gln Leu Leu Ala His Met
45                  50                  55                  60 cag gag gag ggt gtc atc cgc aag ctg aag aaa tat gac aac tg           6118
Gln Glu Glu Gly Val Ile Arg Lys Leu Lys Lys Tyr Asp Asn Cys
                65                  70                  75 gtgagtcccc tcagccctaa ctctctggcc cacagcctcc ctaactctat cttcttagcg    6178
tttggagaat gaagaccttg ccgtagcaaa cacctgagaa gcttaagaga tgccctgtga    6238
ggttagcata gccagccact agattctgga taactataca aagcaactcc ttccccaggg    6298
ccaggtcaca gtctagctaa tgtccacctg gtcaagctcc tgttgtcctt gtttcccgca    6358
aggcttggaa ggacctggcg tgggcaagag aggtacatcc ccgaggatac cttgctgaag    6418
gagtccctgt gacttttca g t tgg ctg gct ctc act gac cct cga gat gtg    6470
                        Trp Leu Ala Leu Thr Asp Pro Arg Asp Val
                                    80                      85 gcc agg atc gaa agc aag aca gtc atc atc acc caa gag cag aga gac      6518
Ala Arg Ile Glu Ser Lys Thr Val Ile Ile Thr Gln Glu Gln Arg Asp
        90                  95                  100 aca gtg ccc atc ccc aaa act ggc ctc agc cag ctg ggc cgc tgg atg      6566
Thr Val Pro Ile Pro Lys Thr Gly Leu Ser Gln Leu Gly Arg Trp Met
    105                 110                 115 tcg gaa gag gac ttt gag aaa gca ttc aac gcc agg ttc cca ggg tgc      6614
Ser Glu Glu Asp Phe Glu Lys Ala Phe Asn Ala Arg Phe Pro Gly Cys
120                 125                 130 atg aaa g gtgggtgaga ccagacccca ggcctgacag tgtgctgtgt acatagttca     6671
Met Lys
    135 tgttcctaat ggcgacctga gctgcaaagc gtggcccacg tgtgaagtgc actgtctggt    6731 tctgtttcat gggtggtgac acacaggaat attaaaatgt tctctgcaag tcctggtggc    6791 tcaggcctgt cagcccagac acggaagccg aggcaggagc attccaagtt tctgccagcc    6851 tgagcaattt acacttggtc tcaaaagaaa aactcaaaag gtagctgtag ctatggttcc    6911 gtggtagagt gtttgcctag aatttccaag gccctgggtt caatccttaa tagacaaaat    6971 agaaaataca taaatgctt cccacccatg tggatgttaa gctgcctaac aggagggtta    7031 tgaaaagttt aatttcagca ctttgcagtt tccgacggcc tcctagacca gaggttcgtg    7091 gccaaaaggc atgatgtgga agacacggct gtgggtacca ttaggaggag gcgccgagga    7151
```

```
tgctcagtgg gcctccgtga cttcttacct atttctgcca acccgcctct gcag gc          7207
                                                             Gly cgc acc atg tat gtc atc cca ttc agc atg ggg cca ctg ggc tcg ccg         7255
Arg Thr Met Tyr Val Ile Pro Phe Ser Met Gly Pro Leu Gly Ser Pro
            140                 145                 150 ctg gcc aag att ggt att gaa ctg aca gac tcg ccc tat gtg gtg gcc         7303
Leu Ala Lys Ile Gly Ile Glu Leu Thr Asp Ser Pro Tyr Val Val Ala
        155                 160                 165 agc atg cgg atc atg act cgg atg ggc ata tct gtg ctg gag gcc ctg         7351
Ser Met Arg Ile Met Thr Arg Met Gly Ile Ser Val Leu Glu Ala Leu
    170                 175                 180 gga gat ggg gag ttc atc aag tgc ctg cac tct gtg ggg tgc cct ctc         7399
Gly Asp Gly Glu Phe Ile Lys Cys Leu His Ser Val Gly Cys Pro Leu
185                 190                 195                 200 ccc tta aaa a gtaagtacat tctttccaga tcgaaggtgg aggagaagt                7449
Pro Leu Lys tggggaaggg ttcagcgggt ggggtgctct cctggcgtgc atgaggccct gagtttgatc       7509
ccagacacca aataaactga acatgctggg tcaggcctac cacccagca cgcaggagtc        7569 aggagaacca gaagtttcag gtccttctca gctccgtagc tggttcgagg ccagcctgga       7629
gacttgggca gggatgtgca ccacaagctc actgtggctt gcttgtttgc ag ag cct        7686
                                                          Lys Pro
                                                              205 ttg gtc aac aac tgg gcc tgc aac cct gag ctg acc ctg atc gcc cac         7734
Leu Val Asn Asn Trp Ala Cys Asn Pro Glu Leu Thr Leu Ile Ala His
        210                 215                 220 ctc ccg gac cgc aga gag atc atc tcc ttt gga agc gga tat ggt ggg         7782
Leu Pro Asp Arg Arg Glu Ile Ile Ser Phe Gly Ser Gly Tyr Gly Gly
    225                 230                 235 aac tca cta ctc ggg aag aaa tgc ttt gcg ttg cgg atc gcc agc cgt         7830
Asn Ser Leu Leu Gly Lys Lys Cys Phe Ala Leu Arg Ile Ala Ser Arg
240                 245                 250 ctg gct aag gag gaa ggg tgg ctg gcg gag cat atg ctg gtatgtggtc          7879
Leu Ala Lys Glu Glu Gly Trp Leu Ala Glu His Met Leu
        255                 260                 265 agggaaccct gggaggaaat ttggagggcc tggggtggca taggtgagct atgtcaaggt       7939
tccccaacat ctggggactt gagggcagag tggagcaata ccaagttgac tctaagtacc      7999
ccagcgtttg tctctttgaa agggactcag acacactggg gctgcagtga ccctggggga      8059
ttttattctt tggtacccca ttagtttatc ctgatgcgtg agggatggat catggcgatc      8119
tgcctttggg aagaccctac gcgctttccc agacctttgc tgcaggaagg aacacagatc      8179
ttcctttctt agacaacagc accgaactca acccctccc ccacctccct cccatttatt       8239
cctcagcatc ttccttttca ttttctgccc cctcccaccc tccgctagtt tggaagacag      8299
tcctaggttt atgttgaaga tacacaccct tcatttctct cttttaccat atgaaggata      8359
cagagtaatg ggttttattg tgagttttct acatgcatgc caaggaccag agacgactaa      8419
agctgatccc gtccatccct gcag atc ctg ggc ata act aac ccc gaa ggc         8470
                         Ile Leu Gly Ile Thr Asn Pro Glu Gly
                                         270                 275 aag aag aaa tac ctg gcc gca gcc ttc cct agt gcc tgt ggg aag act         8518
Lys Lys Lys Tyr Leu Ala Ala Ala Phe Pro Ser Ala Cys Gly Lys Thr
            280                 285                 290 aac ttg gcc atg atg aac ccc agc ctg ccc ggg tgg aag gtc gaa tgt         8566
Asn Leu Ala Met Met Asn Pro Ser Leu Pro Gly Trp Lys Val Glu Cys
        295                 300                 305
```

```
gtg ggc gat gac att gcc tgg atg aag ttt gat gcc caa g gtgagtcttc         8616
Val Gly Asp Asp Ile Ala Trp Met Lys Phe Asp Ala Gln
    310                 315                 320 aggtctggcc aatgacagtg gtggcccctg gtgagtggct ggcttcaaac acactacacc        8676
acagtctcct aaactgtcag caccgggcat tcagggtgag caaggccttc gcagtgctgt        8736
cctgccggcc ttcggtgagg atcatctgga tagagaggga catgataggc tgtttgcttg        8796
cacagatcca tgtttgtacg atgtggctgg ggccaccgag acaagtctat gggtaaaggc        8856
acttgctgcc aagcttaatg atctgagttt gagtcccaga agcctaaatg gtcggaagag        8916
agaactgatt cctgcaagtt atcctccgac ctccatatgt gtgccccaga acactcactc        8976
acacacacac acacacacac acacacacac acacacacac acacactcac acacactcac        9036
acatacacac acacacacac acactcacac acactcacac atacactcac acacactcac        9096
acacacacac tcacatagtc acacacacat acactcacac acacactcac acacacactc        9156
acatagtcac acacacacac acaccacaaa ataaataata atactttaa aagaagagaa         9216 tgtgttttag gaaccgtgaa gaagcagaaa actgcagagt ctgagctgtg gtgtgtagat        9276
caaaatggct ggctgtgtag tttagggacg ggaaagaaaa agatgtgaac tttaggacat        9336
gagctagcct gggcaaagct ttaagaactc tgggatgctt ggcttgcatt catacctcct        9396
tctctgcctg caactttcca g gc aac tta agg gct atc aac cca gaa aac          9446
                        Gly Asn Leu Arg Ala Ile Asn Pro Glu Asn
                                325                 330 ggg ttt ttt gga gtt gct cct ggc acc tca gtg aag aca aat cca aat         9494
Gly Phe Phe Gly Val Ala Pro Gly Thr Ser Val Lys Thr Asn Pro Asn
            335                 340                 345 gcc att aaa acc atc cag aaa aac acc atc ttc acc aac gtg gcc gag         9542
Ala Ile Lys Thr Ile Gln Lys Asn Thr Ile Phe Thr Asn Val Ala Glu
        350                 355                 360 act agc gat ggg ggt gtt tac tgg gaa ggc atc gat gag ccg ctg gcc         9590
Thr Ser Asp Gly Gly Val Tyr Trp Glu Gly Ile Asp Glu Pro Leu Ala
    365                 370                 375 ccg gga gtc acc atc acc tcc tgg aag aac aag gag tgg aga ccg cag         9638
Pro Gly Val Thr Ile Thr Ser Trp Lys Asn Lys Glu Trp Arg Pro Gln
    380                 385                 390 gac g gtgagtccct cgagaggctg tgtgctctgg cttctgggtg ccacctatct             9692
Asp
395 gggccatgct aaggggtatc tctctcgttc tctctcttgc ag cg gaa cca tgt gcc        9748
                                                Ala Glu Pro Cys Ala
                                                              400 cat ccc aac tcg aga ttc tgc acc cct gcc agc cag tgc ccc att att         9796
His Pro Asn Ser Arg Phe Cys Thr Pro Ala Ser Gln Cys Pro Ile Ile
        405                 410                 415 gac cct gcc tgg gaa tct cca gaa gga gta ccc att gag ggt atc atc         9844
Asp Pro Ala Trp Glu Ser Pro Glu Gly Val Pro Ile Glu Gly Ile Ile
        420                 425                 430 ttt ggt ggc cgt aga cct gaa g gtgaggcatc ttctattcag gctgggaacc          9896
Phe Gly Gly Arg Arg Pro Glu
            435 tggggtgtgg cgatgcaaag aaatccagga aatatttttc caagctggtt ccaaaggatc       9956 tcctcctata cttccagact aactgggcag ttttaaacat agggccagcc ttctgatcac      10016 caatggcttc tgtgggtctg tgatctgagg tagctcaggt tgttctgctc cactgagtga      10076 tctctctgct gtgactgccc ttagcggttt cctgttcatt gtctctctag gtgaaaggtt      10136 aactcaacag aaaactcggc ttgtcagacc tagagtggct cacagctgta atcctagcac      10196
```

```
                                       -continued ttgggtggct ggggcagggg gattgctttg agttcaggtg tggcctggtc tacagagtaa    10256
gctccaggct atcttgggct accgagtgaa actttctcat caaaacaaaa caagcaagga    10316
aggaaggaag gaaggaagga aggaaggaag gaaggaaggg aagaaggaag gaggaaggaa    10376
ggaaggaagg aaggaaggaa ggaaggaagg aaggaaggag ggaaggaaag atacagcatg    10436
gttgaacagt gacgatagaa ctaagatgtc ctaagtcttt aatgatcttt gtctccctgc    10496 tcaag gt gtc ccc ctt gtc tat gaa gcc ctc agc tgg cag cat ggg gtg     10545
      Gly Val Pro Leu Val Tyr Glu Ala Leu Ser Trp Gln His Gly Val
          440             445                 450 ttt gta gga gca gcc atg aga tct gag gcc aca gct gct gca gaa cac      10593
Phe Val Gly Ala Ala Met Arg Ser Glu Ala Thr Ala Ala Ala Glu His
455             460                 465                 470 aag g gtgagtcaca gtctacaacc caaaccctct tcttggtgtc tgtcaggag           10647
Lys ggagaaatct ggcctgattg ggtcagaggt aaatggtggt ctctctgtgg cag gc aag     10705
                                                         Gly Lys atc atc atg cac gac ccc ttt gcc atg cga ccc ttc ttc ggc tac aac      10753
Ile Ile Met His Asp Pro Phe Ala Met Arg Pro Phe Phe Gly Tyr Asn
    475             480                 485 ttc ggc aaa tac ctg gcc cac tgg ctg agc atg gcc cac cgc cca gca      10801
Phe Gly Lys Tyr Leu Ala His Trp Leu Ser Met Ala His Arg Pro Ala
490             495                 500                 505 gcc aag ttg ccc aag atc ttc cat gtc aac tgg ttc cgg aag gac aaa      10849
Ala Lys Leu Pro Lys Ile Phe His Val Asn Trp Phe Arg Lys Asp Lys
                510             515                 520 gat ggc aag ttc ctc tgg cca ggc ttt ggc gag aac tcc cgg gtg ctg      10897
Asp Gly Lys Phe Leu Trp Pro Gly Phe Gly Glu Asn Ser Arg Val Leu
                525             530                 535 gag tgg atg ttc ggg cgg att gaa ggg gaa gac agc gcc aag ctc acg      10945
Glu Trp Met Phe Gly Arg Ile Glu Gly Glu Asp Ser Ala Lys Leu Thr
                540             545                 550 ccc atc ggc tac atc cct aag gaa aac gcc ttg aac ctg aaa ggc ctg      10993
Pro Ile Gly Tyr Ile Pro Lys Glu Asn Ala Leu Asn Leu Lys Gly Leu
    555             560                 565 ggg ggc gtc aac gtg gag gag ctg ttt ggg atc tct aag gag ttc tgg      11041
Gly Gly Val Asn Val Glu Glu Leu Phe Gly Ile Ser Lys Glu Phe Trp
570             575                 580                 585 gag aag gag gtg gag gag atc gac agg tat ctg gag gac cag gtc aac      11089
Glu Lys Glu Val Glu Glu Ile Asp Arg Tyr Leu Glu Asp Gln Val Asn
                590             595                 600 acc gac ctc cct tac gaa att gag agg gag ctc cga gcc ctg aaa cag      11137
Thr Asp Leu Pro Tyr Glu Ile Glu Arg Glu Leu Arg Ala Leu Lys Gln
                605             610                 615 aga atc agc cag atg taa atcccaatgg gggcgtctcg agagtcaccc              11185
Arg Ile Ser Gln Met
        620 cttcccactc acagcatcgc tgagatctag gagaaagcca gcctgctcca gctttgagat    11245 agcggcacaa tcgtgagtag atcagaaaag cacccttttaa tagtcagttg agtagcacag   11305 agaacaggct agggggcaaat aagattggga ggggaaatca ccgcatagtc tctgaagttt   11365 gcatttgaca ccaatggggg ttttggttcc acttcaaggt cactcaggaa tccagttctt    11425 cacgttagct gtagcagtta gctaaaatgc acagaaaaca tacttgagct gtatatatgt    11485 gtgtgaacgt gtctctgtgt gagcatgtgt gtgtgtgtgt gtgtgtgtgt gtgtgtgtgt    11545 gtgtgtgtgt gtgtacatgc ctgtctgtcc cattgtccac agtatattta aaacctttgg   11605 ggaaaaatct tgggcaaatt tgtagctgta actagagagt catgttgctt tgttgctagt    11665
```

```
atgtatgttt aaattatttt tatacaccgc ccttaccttt ctttacataa ttgaaattgg   11725
tatccggacc acttcttggg aaaaaaatta caaaataaac ttttatagaa aaagtagatt   11785
tcattgcctc tttttggttt ttattagaaa gggagaacac actgattaaa caccctgggg   11845
ctctaatctt gctcccccgg gagcctgggg gattcacagc tgaaaggagg ggacttgtca   11905
ggggccagat gtatgaggga cgggatgtgt gagggaccgg aaggagggga gaaagcagag   11965
caccggcttc ccatgttata aaacattgtt accactagtt ggcgctcttt ggcagcgttt   12025
cgggacaggt ctgtgcgttt gcacagctgg atctagaggg tttaaggtga attttaaaga   12085
gagtttgagc ctcagggctc agccatctcc aaaagtgcag tgtgaacaag cacagg       12141
```

```
<210> SEQ ID NO 11
<211> LENGTH: 17
<212> TYPE: DNA
<213> ORGANISM: Artificial Sequence
<220> FEATURE:
<223> OTHER INFORMATION: PCR Primer

<400> SEQUENCE: 11
atccagggca gcctcga                                                  17

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
agcattgcct tccacgaact                                               20

<210> SEQ ID NO 13
<211> LENGTH: 21
<212> TYPE: DNA
<213> ORGANISM: Artificial Sequence
<220> FEATURE:
<223> OTHER INFORMATION: PCR Probe

<400> SEQUENCE: 13
agcctgcccc aggcagtgag g                                             21

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                               20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagct                                               20

<210> SEQ ID NO 16
<211> LENGTH: 27
```

```
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                              27

<210> SEQ ID NO 17
<211> LENGTH: 2618
<212> TYPE: DNA
<213> ORGANISM: Mus musculus
<220> FEATURE:
<221> NAME/KEY: CDS
<222> LOCATION: (141)...(2009)

<400> SEQUENCE: 17
acagttggcc ttccctctgg gaacacaccc tcggtcaaca ggggaaatcc ggcaaggcgc          60
tcagcgatct ctgatccaga ccttccaaaa ggaagaaagg tggcaccaga gttcctgcct        120
ctctccacac cattgcaatt atg cct cct cag ctg cat aac ggt ctg gac            170
                        Met Pro Pro Gln Leu His Asn Gly Leu Asp
                         1               5                  10 ttc tct gcc aag gtt atc cag ggc agc ctc gac agc ctg ccc cag gca         218
Phe Ser Ala Lys Val Ile Gln Gly Ser Leu Asp Ser Leu Pro Gln Ala
             15                  20                  25 gtg agg aag ttc gtg gaa ggc aat gct cag ctg tgc cag ccg gag tat         266
Val Arg Lys Phe Val Glu Gly Asn Ala Gln Leu Cys Gln Pro Glu Tyr
         30                  35                  40 atc cac atc tgc gat ggc tcc gag gag gag tac ggg cag ttg ctg gcc         314
Ile His Ile Cys Asp Gly Ser Glu Glu Glu Tyr Gly Gln Leu Leu Ala
     45                  50                  55 cac atg cag gag gag ggt gtc atc cgc aag ctg aag aaa tat gac aac         362
His Met Gln Glu Glu Gly Val Ile Arg Lys Leu Lys Lys Tyr Asp Asn
 60                  65                  70 tgt tgg ctg gct ctc act gac cct cga gat gtg gcc agg atc gaa agc         410
Cys Trp Leu Ala Leu Thr Asp Pro Arg Asp Val Ala Arg Ile Glu Ser
 75                  80                  85                  90 aag aca gtc atc atc acc caa gag cag aga gac aca gtg ccc atc ccc         458
Lys Thr Val Ile Ile Thr Gln Glu Gln Arg Asp Thr Val Pro Ile Pro
                 95                 100                 105 aaa act ggc ctc agc cag ctg ggc cgc tgg atg tcg gaa gag gac ttt         506
Lys Thr Gly Leu Ser Gln Leu Gly Arg Trp Met Ser Glu Glu Asp Phe
             110                 115                 120 gag aaa gca ttc aac gcc agg ttc cca ggg tgc atg aaa ggc cgc acc         554
Glu Lys Ala Phe Asn Ala Arg Phe Pro Gly Cys Met Lys Gly Arg Thr
         125                 130                 135 atg tat gtc atc cca ttc agc atg ggg cca ctg ggc tcg ccg ctg gcc         602
Met Tyr Val Ile Pro Phe Ser Met Gly Pro Leu Gly Ser Pro Leu Ala
     140                 145                 150 aag att ggt att gaa ctg aca gac tcg ccc tat gtg gtg gcc agc atg         650
Lys Ile Gly Ile Glu Leu Thr Asp Ser Pro Tyr Val Val Ala Ser Met
155                 160                 165                 170 cgg atc atg act cgg atg ggc ata tct gtg ctg gag gcc ctg gga gat         698
Arg Ile Met Thr Arg Met Gly Ile Ser Val Leu Glu Ala Leu Gly Asp
             175                 180                 185 ggg gag ttc atc aag tgc ctg cac tct gtg ggg tgc cct ctc ccc tta         746
Gly Glu Phe Ile Lys Cys Leu His Ser Val Gly Cys Pro Leu Pro Leu
         190                 195                 200 aaa aag cct ttg gtc aac aac tgg gcc tgc aac cct gag ctg acc ctg         794
Lys Lys Pro Leu Val Asn Asn Trp Ala Cys Asn Pro Glu Leu Thr Leu
     205                 210                 215
```

-continued

| | |
|---|---|
| atc gcc cac ctc ccg gac cgc aga gag atc atc tcc ttt gga agc gga<br>Ile Ala His Leu Pro Asp Arg Arg Glu Ile Ile Ser Phe Gly Ser Gly<br>220                          225                    230 | 842 |
| tat ggt ggg aac tca cta ctc ggg aag aaa tgc ttt gcg ttg cgg atc<br>Tyr Gly Gly Asn Ser Leu Leu Gly Lys Lys Cys Phe Ala Leu Arg Ile<br>235                  240                    245                  250 | 890 |
| gcc agc cgt ctg gct aag gag gaa ggg tgg ctg gcg gag cat atg ctg<br>Ala Ser Arg Leu Ala Lys Glu Glu Gly Trp Leu Ala Glu His Met Leu<br>                  255                    260                  265 | 938 |
| atc ctg ggc ata act aac ccc gaa ggc aag aag aaa tac ctg gcc gca<br>Ile Leu Gly Ile Thr Asn Pro Glu Gly Lys Lys Lys Tyr Leu Ala Ala<br>270                          275                    280 | 986 |
| gcc ttc cct agt gcc tgt ggg aag act aac ttg gcc atg atg aac ccc<br>Ala Phe Pro Ser Ala Cys Gly Lys Thr Asn Leu Ala Met Met Asn Pro<br>                  285                    290                  295 | 1034 |
| agc ctg ccc ggg tgg aag gtc gaa tgt gtg ggc gat gac att gcc tgg<br>Ser Leu Pro Gly Trp Lys Val Glu Cys Val Gly Asp Asp Ile Ala Trp<br>300                          305                    310 | 1082 |
| atg aag ttt gat gcc caa ggc aac tta agg gct atc aac cca gaa aac<br>Met Lys Phe Asp Ala Gln Gly Asn Leu Arg Ala Ile Asn Pro Glu Asn<br>315                          320                    325                  330 | 1130 |
| ggg ttt ttt gga gtt gct cct ggc acc tca gtg aag aca aat cca aat<br>Gly Phe Phe Gly Val Ala Pro Gly Thr Ser Val Lys Thr Asn Pro Asn<br>                  335                    340                  345 | 1178 |
| gcc att aaa acc atc cag aaa aac acc atc ttc acc aac gtg gcc gag<br>Ala Ile Lys Thr Ile Gln Lys Asn Thr Ile Phe Thr Asn Val Ala Glu<br>350                          355                    360 | 1226 |
| act agc gat ggg ggt gtt tac tgg gaa ggc atc gat gag ccg ctg gcc<br>Thr Ser Asp Gly Gly Val Tyr Trp Glu Gly Ile Asp Glu Pro Leu Ala<br>                  365                    370                  375 | 1274 |
| ccg gga gtc acc atc acc tcc tgg aag aac aag gag tgg aga ccg cag<br>Pro Gly Val Thr Ile Thr Ser Trp Lys Asn Lys Glu Trp Arg Pro Gln<br>380                          385                    390 | 1322 |
| gac gcg gaa cca tgt gcc cat ccc aac tcg aga ttc tgc acc cct gcc<br>Asp Ala Glu Pro Cys Ala His Pro Asn Ser Arg Phe Cys Thr Pro Ala<br>395                          400                    405                  410 | 1370 |
| agc cag tgc ccc att att gac cct gcc tgg gaa tct cca gaa gga gta<br>Ser Gln Cys Pro Ile Ile Asp Pro Ala Trp Glu Ser Pro Glu Gly Val<br>                  415                    420                  425 | 1418 |
| ccc att gag ggt atc atc ttt ggt ggc cgt aga cct gaa ggt gtc ccc<br>Pro Ile Glu Gly Ile Ile Phe Gly Gly Arg Arg Pro Glu Gly Val Pro<br>430                          435                    440 | 1466 |
| ctt gtc tat gaa gcc ctc agc tgg cag cat ggg gtg ttt gta gga gca<br>Leu Val Tyr Glu Ala Leu Ser Trp Gln His Gly Val Phe Val Gly Ala<br>                  445                    450                  455 | 1514 |
| gcc atg aga tct gag gcc aca gct gct gca gaa cac aag ggc aag atc<br>Ala Met Arg Ser Glu Ala Thr Ala Ala Ala Glu His Lys Gly Lys Ile<br>460                          465                    470 | 1562 |
| atc atg cac gac ccc ttt gcc atg cga ccc ttc ttc ggc tac aac ttc<br>Ile Met His Asp Pro Phe Ala Met Arg Pro Phe Phe Gly Tyr Asn Phe<br>475                          480                    485                  490 | 1610 |
| ggc aaa tac ctg gcc cac tgg ctg agc atg gcc cac cgc cca gca gcc<br>Gly Lys Tyr Leu Ala His Trp Leu Ser Met Ala His Arg Pro Ala Ala<br>                  495                    500                  505 | 1658 |
| aag ttg ccc aag atc ttc cat gtc aac tgg ttc cgg aag gac aaa gat<br>Lys Leu Pro Lys Ile Phe His Val Asn Trp Phe Arg Lys Asp Lys Asp<br>510                          515                    520 | 1706 |
| ggc aag ttc ctc tgg cca ggc ttt ggc gag aac tcc cgg gtg ctg gag<br>Gly Lys Phe Leu Trp Pro Gly Phe Gly Glu Asn Ser Arg Val Leu Glu<br>                  525                    530                  535 | 1754 |

| | | | | | | | | | | | | |
|---|---|---|---|---|---|---|---|---|---|---|---|---|
| tgg | atg | ttc | ggg | cgg | att | gaa | ggg | gaa | gac | agc | gcc | aag | ctc | acg | ccc | 1802 |
| Trp | Met | Phe | Gly | Arg | Ile | Glu | Gly | Glu | Asp | Ser | Ala | Lys | Leu | Thr | Pro | |
| | 540 | | | | | 545 | | | | | 550 | | | | | |

| atc | ggc | tac | atc | cct | aag | gaa | aac | gcc | ttg | aac | ctg | aaa | ggc | ctg | ggg | 1850 |
| Ile | Gly | Tyr | Ile | Pro | Lys | Glu | Asn | Ala | Leu | Asn | Leu | Lys | Gly | Leu | Gly | |
| 555 | | | | | 560 | | | | | 565 | | | | | 570 | |

| ggc | gtc | aac | gtg | gag | gag | ctg | ttt | ggg | atc | tct | aag | gag | ttc | tgg | gag | 1898 |
| Gly | Val | Asn | Val | Glu | Glu | Leu | Phe | Gly | Ile | Ser | Lys | Glu | Phe | Trp | Glu | |
| | | | 575 | | | | | 580 | | | | | 585 | | | |

| aag | gag | gtg | gag | gag | atc | gac | agg | tat | ctg | gag | gac | cag | gtc | aac | acc | 1946 |
| Lys | Glu | Val | Glu | Glu | Ile | Asp | Arg | Tyr | Leu | Glu | Asp | Gln | Val | Asn | Thr | |
| | | 590 | | | | | 595 | | | | | 600 | | | | |

| gac | ctc | cct | tac | gaa | att | gag | agg | gag | ctc | cga | gcc | ctg | aaa | cag | aga | 1994 |
| Asp | Leu | Pro | Tyr | Glu | Ile | Glu | Arg | Glu | Leu | Arg | Ala | Leu | Lys | Gln | Arg | |
| | | 605 | | | | | 610 | | | | | 615 | | | | |

| atc | agc | cag | atg | taa | atcccaatgg | gggcgtctcg | agagtcaccc | cttcccactc | 2049 |
| Ile | Ser | Gln | Met | | | | | | |
| | 620 | | | | | | | | | acagcatcgc tgagatctag gagaaagcca gcctgctcca gctttgagat agcggcacaa 2109 tcgtgagtag atcagaaaag cacctttaa tagtcagttg agtagcacag agaacaggct 2169 agggggcaaat aagattggga ggggaaatca ccgcatagtc tctgaagttt gcatttgaca 2229 ccaatggggg ttttggttcc acttcaaggt cactcaggaa tccagttctt cacgttagct 2289 gtagcagtta gctaaaatgc acagaaaaca tacttgagct gtatatatgt gtgtgaacgt 2349 gtctctgtgt gagcatgtgt gtgtgtgtgt gtgtgtgtgt gtgtgtgtgt gtgtgtgtgt 2409 gtgtacatgc ctgtctgtcc cattgtccac agtatattta aacctttgg ggaaaaatct 2469 tgggcaaatt tgtagctgta actagagagt catgttgctt tgttgctagt atgtatgttt 2529 aaattatttt tatacaccgc ccttaccttt ctttacataa ttgaaattgg tatccggacc 2589 acttcttggg aaaaaaatta caaaataaa 2618

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
ctcttcccgc cagcaagttt                                               20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tggatgatct cgaagggaga                                               20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
tttctgcaga gtgctgctaa                                               20

```
<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
catttctgca gagtgctgct                                          20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ggcatttctg cagagtgctg                                          20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gaggcatttc tgcagagtgc                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
aggaggcatt tctgcagagt                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tgaggaggca tttctgcaga                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gctgaggagg catttctgca                                          20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 27
cagctgagga ggcatttctg                                      20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tgcagctgag gaggcatttc                                      20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tttgcagctg aggaggcatt                                      20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gttttgcagc tgaggaggca                                      20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
ccgttttgca gctgaggagg                                      20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
cgagaggttc aggccgtttt                                      20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gctgtccagg cttccctgga                                      20

<210> SEQ ID NO 34
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 34
gctgacacag ctcagcgtta                                                  20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tcagagccgt cacagatgtg                                                  20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ggcccagaag ccgcccattc                                                  20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ctgaggatgc cctcttcctc                                                  20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gcagttgtca tacttcttca                                                  20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ctttcgatcc tggccacatc                                                  20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 40
gctcttgggt gacgataacc                          20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gctggctgag gcctgttttg                          20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
atcctcctct gacatccagc                          20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ggaacctggc attgaacgct                          20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cgtacatggt gcgaccttte                          20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cagcggcccc atgctgaatg                          20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
agctcgatgc cgatcttcga                          20

<210> SEQ ID NO 47
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 47
catgctggcc accacgtagg                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gacgggcgtg cccatccgcg                                                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ttgacaaact ccccatcgcc                                                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gtaaaggcag agggcacccc                                                    20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gttgcagggc cagttgttga                                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gtcaggcagg tgggcgatga                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 53
ccgtacccac tgccaaagga                                            20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
caaagcactt cttcccgagc                                            20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ttcctcctct gccagccggc                                            20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tatacccaga atcagcatgt                                            20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ccgccaggta cttcttctca                                            20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
aggttggtct tcccgcaggc                                            20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tccaggcaat gtcatccccg                                            20

<210> SEQ ID NO 60
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 60
tgggttgatg gcccttaaat                                                     20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ctggatggtc ttgatggcat                                                     20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cgtcgctggt ctcggccaca                                                     20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cgtgatggtg acgcctgaag                                                     20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ggttccccat cctctgagct                                                     20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
aatgggaaca ccttccggag                                                     20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 66
gggacaccag caggtctacg                                                   20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
aaagactcca tgttgccagc                                                   20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
gattttgcct ttatgttctg                                                   20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ggtatttgcc gaagttgtag                                                   20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tttggctgct gggtgctggg                                                   20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tgtccttccg gaaccagttg                                                   20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ggagttctct ccaaagcctg                                                   20

<210> SEQ ID NO 73
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 73
cttttccatc gatccggttg                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tcaggttcag ggcatcctcc                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gatgctgaaa agctccatca                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tctcgatgtc ttccacctcc                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ggatctctct ctcgatttca                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tcaggccctg attacatctg                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 79
ttaaaggtaa agcactcagg                                                  20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ctactgcacc ttatggattt                                                  20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tggcgtcaat ttgggaacac                                                  20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctgctcccgg tgtggtgatg                                                  20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ccagtgttct gtggttctta                                                  20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
aagatttccc ttctcaattt                                                  20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
aatttgaaca aagtatgcat                                                  20

<210> SEQ ID NO 86
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 86
aacactgaaa agatcaatgc                                          20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
atatatatat acagctcaag                                          20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
acacacacac acacacacac                                          20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tgtgcacata catgcacaca                                          20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
aaatatcaca cagacacatg                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
acaaatacac ataccaaata                                          20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 92
tattttgaat aacagtacat                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
caaaggtatt aaatatattt                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
ggtcatcttg cccaagattt                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
aaggaaaact agtaggtcat                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
ttaagcacaa tattaataac                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
tgtaaaggta aggaacaatg                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ccctgcctac ctttcttcct                                              20

<210> SEQ ID NO 99
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 99 tgtattttg gagaggtgaa                                          20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
aagaacatga gtgggcccct                                         20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
ggaaaacctt ccaagaacat                                         20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
cacttacttt actgggacgg                                         20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gggtattctt gtactcaccc                                         20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
ctcttaagct tctcaggtgt                                         20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 105
ggagcttgac caggtggaca                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
aagtcacagg gactccttca                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tgggccacgc tttgcagctc                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
gaaacagaac cagacagtgc                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
tttcttttga gaccaagtgt                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
aggcagctta acatccacat                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tgcaaagtgc tgaaattaaa                                              20

<210> SEQ ID NO 112
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 112
tgcctttggg ccacgaacct                                          20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
atcatgcctt ttggccacga                                          20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
caaactcagg gcctcatgca                                          20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
tggtaggcct gacccagcat                                          20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
accaaaggct ctgcaaacaa                                          20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
agggtcttcc caaaggcaga                                          20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 118
atggacggga tcagctttag                                                        20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
gaagactcac cttgggcatc                                                        20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
gtgtgtgtga gtgtgtgtga                                                        20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
actctgcagt tttctgcttc                                                        20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
ctagctcatg tcctaaagtt                                                        20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
caagcatccc agagttctta                                                        20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
ggtatgaatg caagccaagc                                                        20

<210> SEQ ID NO 125
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 125
agagaaggag gtatgaatgc                                               20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
agccagagca cacagcctct                                               20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
acgagagaga taccccttag                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
catggttccg ctgcaagaga                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
gatgcctcac cttcaggtct                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
agatcctttg gaaccagctt                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 131 agtttctgt tgagttaacc                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ttccttcctt ccttcctcct                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
ataaaagttt attttgtaat                                              20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
ctataaaagt ttattttgta                                              20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
gtgttcccag agggaaggcc                                              20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
tgagcgcctt gccggatttc                                              20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ctggtgccac ctttcttcct                                              20

<210> SEQ ID NO 138
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 138
ttgcaatggt gtggagagag                                              20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
gcataattgc aatggtgtgg                                              20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
ctgaggaggc ataattgcaa                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
agatgtggat atactccggc                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
atgacaccct cctcctgcat                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
agccagccaa cagttgtcat                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 144
cttgggtgat gatgactgtc                                          20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
tctctgctct tgggtgatga                                          20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ccagctggct gaggccagtt                                          20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
tttctcaaag tcctcttccg                                          20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
caccctggga acctggcgtt                                          20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
atggtgcggc ctttcatgca                                          20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tgaatgggat gacatacatg                                          20

<210> SEQ ID NO 151
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 151
tgctgaatgg gatgacatac                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ctccttagcc agacggctgg                                               20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
cttaagttgc cttgggcatc                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
aaaaacccgt tttctgggtt                                               20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
atttggattt gtcttcactg                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agtctcggcc acgttggtga                                               20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 157
aaacaccccc atcgctagtc                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
catcgatgcc ttcccagtaa                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
caaagatgat accctcaatg                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tctgcagcag ctgtggcctc                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
atgatcttgc ccttgtgttc                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
gtatttgccg aagttgtagc                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
ggccatgctc agccagtggg                                              20

<210> SEQ ID NO 164
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 164
ccagaggaac ttgccatctt                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
tccgcccgaa catccactcc                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
gtagccgatg ggcgtgagct                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
tcaatttcgt aagggaggtc                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
gattctctgt ttcagggctc                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
attgggattt acatctggct                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 170
aaaggtgctt ttctgatcta                                                           20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tattaaaagg tgcttttctg                                                           20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
tggaaccaaa accccattg                                                            20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
ttttctgtgc attttagcta                                                           20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
gctcaagtat gttttctgtg                                                           20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
cacatgctca cacagagaca                                                           20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
tacaaatttg cccaagattt                                                           20

<210> SEQ ID NO 177
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 177
aaacatacat actagcaaca                                                   20
```